US011540896B2

(12) United States Patent
Chang et al.

(10) Patent No.: US 11,540,896 B2
(45) Date of Patent: Jan. 3, 2023

(54) STEERABLE GUIDE FOR MINIMALLY INVASIVE SURGERY

(71) Applicant: UNIVERSITY OF MIAMI, Miami, FL (US)

(72) Inventors: Doyoung Chang, Miami, FL (US); Iahn Cajigas, Miami, FL (US); Michael E. Ivan, Miami, FL (US)

(73) Assignee: UNIVERSITY OF MIAMI, Miami, FL (US)

( * ) Notice: Subject to any disclaimer, the term of this patent is extended or adjusted under 35 U.S.C. 154(b) by 0 days.

(21) Appl. No.: 17/616,112

(22) PCT Filed: Jun. 2, 2020

(86) PCT No.: PCT/US2020/035770
§ 371 (c)(1),
(2) Date: Dec. 2, 2021

(87) PCT Pub. No.: WO2020/247402
PCT Pub. Date: Dec. 10, 2020

(65) Prior Publication Data
US 2022/0211459 A1    Jul. 7, 2022

Related U.S. Application Data

(60) Provisional application No. 62/856,487, filed on Jun. 3, 2019.

(51) Int. Cl.
*A61B 90/11* (2016.01)
*A61B 18/22* (2006.01)
(Continued)

(52) U.S. Cl.
CPC .............. *A61B 90/11* (2016.02); *A61B 18/22* (2013.01); *A61B 2018/00011* (2013.01);
(Continued)

(58) Field of Classification Search
CPC ................... A61B 90/10; A61B 90/11; A61B 2018/00053; A61B 2018/00059;
(Continued)

(56) References Cited

U.S. PATENT DOCUMENTS

| 3,452,740 | A |   | 7/1969 | Muller |
| 5,308,324 | A | * | 5/1994 | Hammerslag ..... A61M 25/0144 |
|   |   |   |   | 604/528 |

(Continued)

FOREIGN PATENT DOCUMENTS

WO    WO-2020247402 A1 * 12/2020    ............. A61B 18/00

OTHER PUBLICATIONS

International Search Report and Written Opinion for corresponding PCT/US2020/35770, dated Aug. 31, 2020 in 12 pages.

*Primary Examiner* — Ahmed M Farah
(74) *Attorney, Agent, or Firm* — Procopio, Cory, Hargreaves & Savitch LLP

(57) ABSTRACT

A steerable guide. In an embodiment, the steerable guide comprises a needle, a shaft, a spring housing, and a translational screw. The needle comprises a wire tube and a wire configured to curve the needle when retracted relative to the wire tube. The wire tube is connected to the distal end of the shaft, and the wire is connected to the distal end of the spring housing. The screw extends into a cavity within the shaft, and is configured to move along a longitudinal axis. A spring is positioned within the cavity, between the proximal end of the spring housing and the distal end of the screw. Thus, when the screw moves in the proximal direction while a position of the spring housing is fixed by the wire, the spring is compressed between the proximal end of the spring housing and the distal end of the translational screw.

21 Claims, 25 Drawing Sheets

(51) Int. Cl.
    *A61B 18/00*        (2006.01)
    *A61M 25/01*        (2006.01)
    *A61M 25/06*        (2006.01)

(52) U.S. Cl.
    CPC ............ *A61B 2018/00577* (2013.01); *A61M 25/0147* (2013.01); *A61M 25/065* (2013.01); *A61M 2205/0266* (2013.01)

(58) Field of Classification Search
    CPC ........... A61B 2018/00184; A61B 2018/00196; A61B 2018/00577; A61B 18/22; A61B 2018/2238; A61B 18/24; A61B 18/245; A61M 25/01; A61M 25/0102; A61M 25/0105; A61M 25/0133; A61M 25/0147; A61M 25/015; A61M 25/018; A61M 25/06; A61M 25/0612; A61M 25/065; A61M 2025/0681; A61M 2025/09058; A61M 2025/09091; A61M 2025/09125; A61M 2025/09133
    USPC .............................................. 606/1, 15, 130
    See application file for complete search history.

(56) References Cited

U.S. PATENT DOCUMENTS

| | | | |
|---|---|---|---|
| 6,132,390 A * | 10/2000 | Cookston | A61M 25/0155 600/585 |
| 6,554,794 B1 * | 4/2003 | Mueller | A61M 25/0141 604/95.04 |
| 7,998,112 B2 * | 8/2011 | Chow | A61M 25/0152 604/93.01 |
| 11,083,871 B2 * | 8/2021 | Curley | A61M 25/0074 |
| 2004/0133168 A1 * | 7/2004 | Salcudean | A61B 17/3478 604/164.13 |
| 2009/0131948 A1 * | 5/2009 | Liu | A61M 25/0152 606/92 |
| 2016/0100860 A1 * | 4/2016 | Lenker | A61B 17/3478 604/95.01 |
| 2019/0374746 A1 * | 12/2019 | Konh | A61B 34/30 |

* cited by examiner

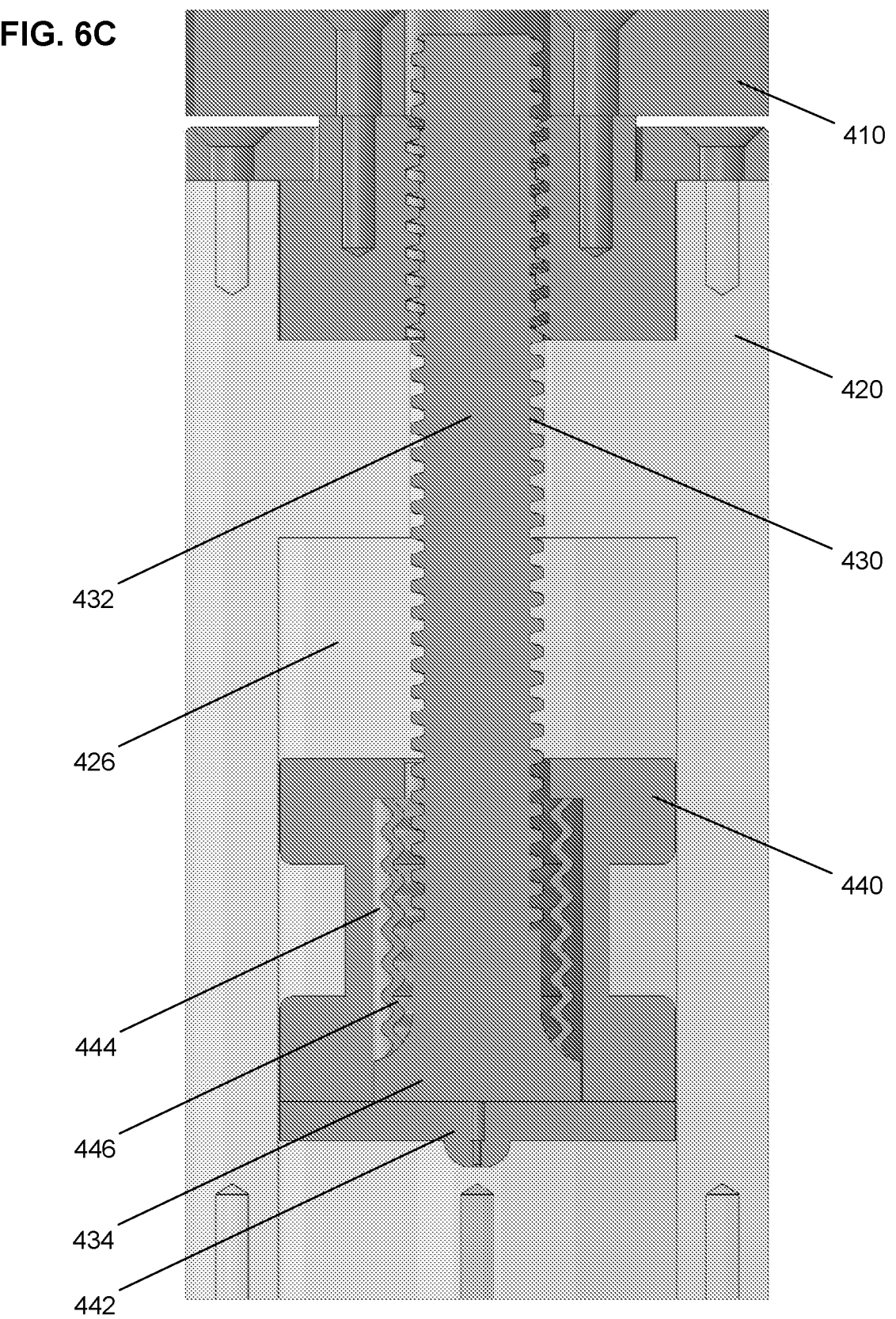

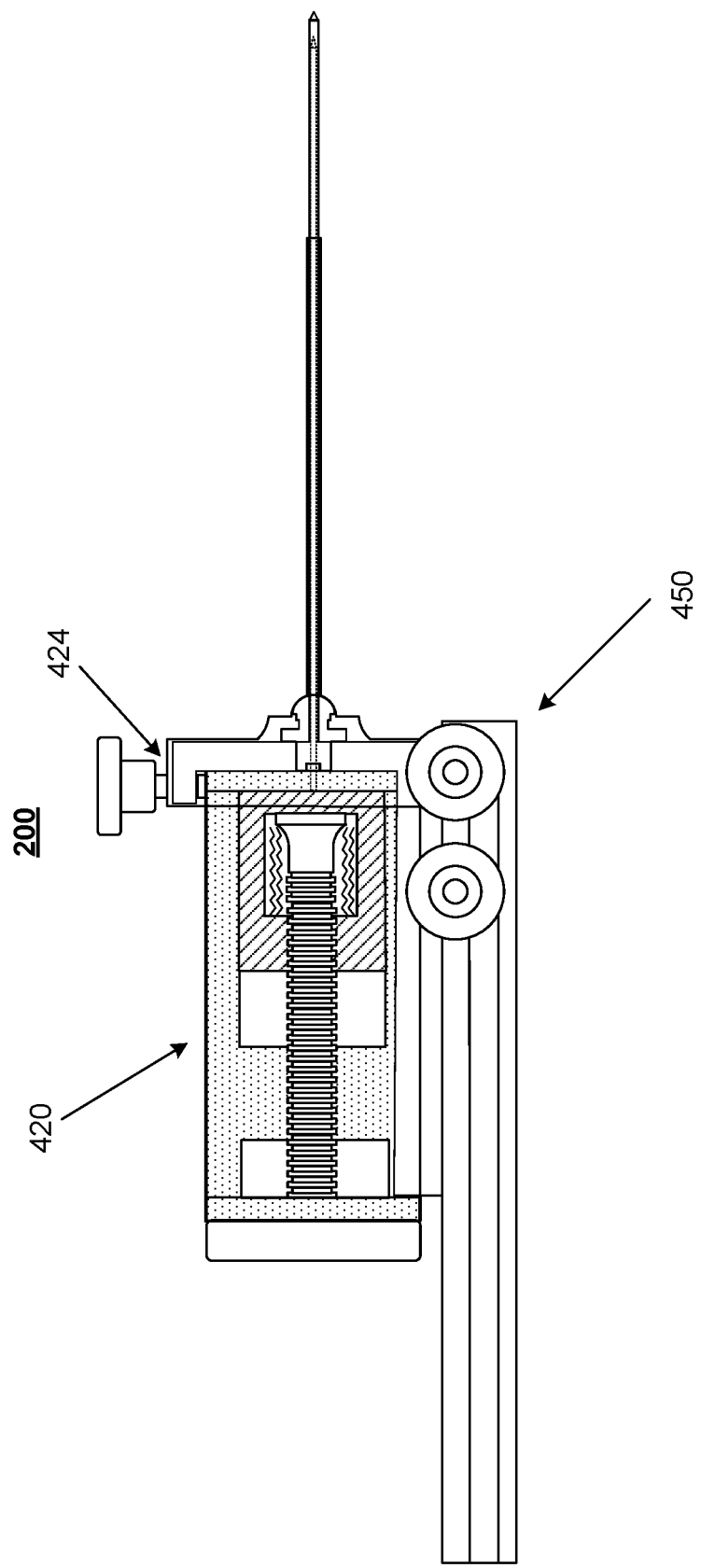

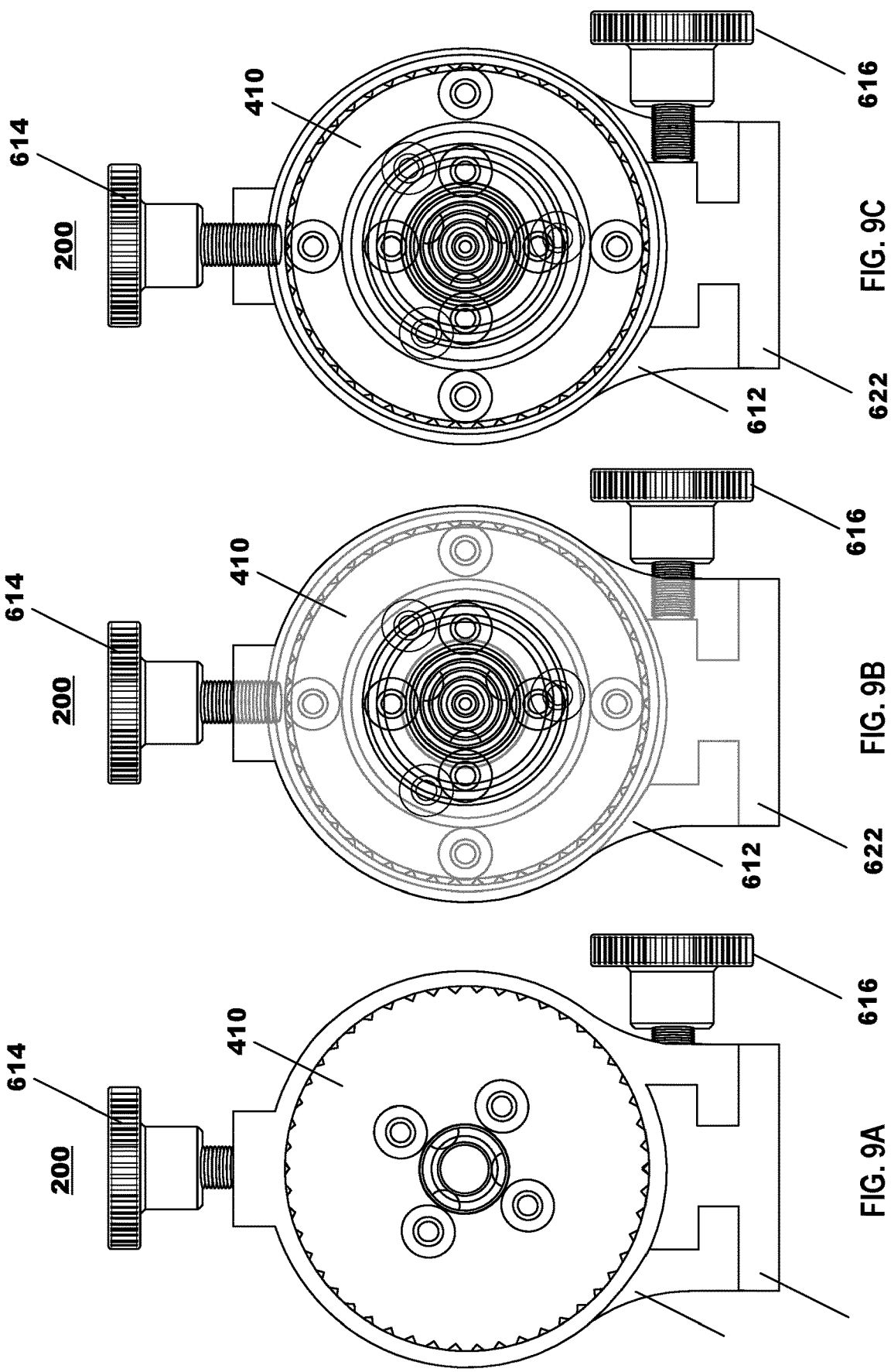

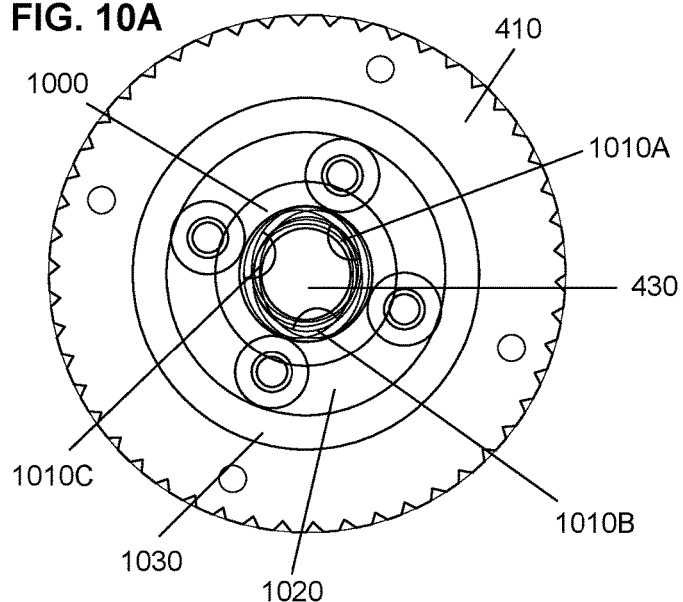
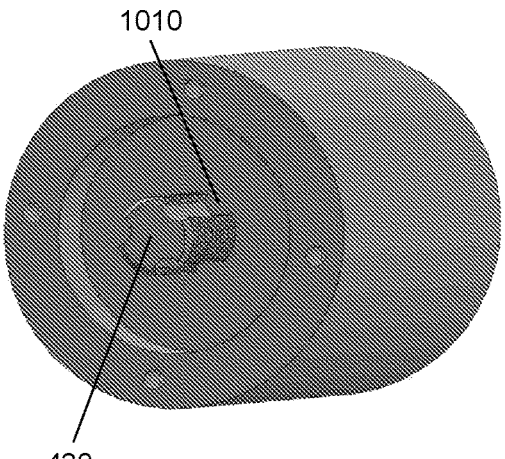
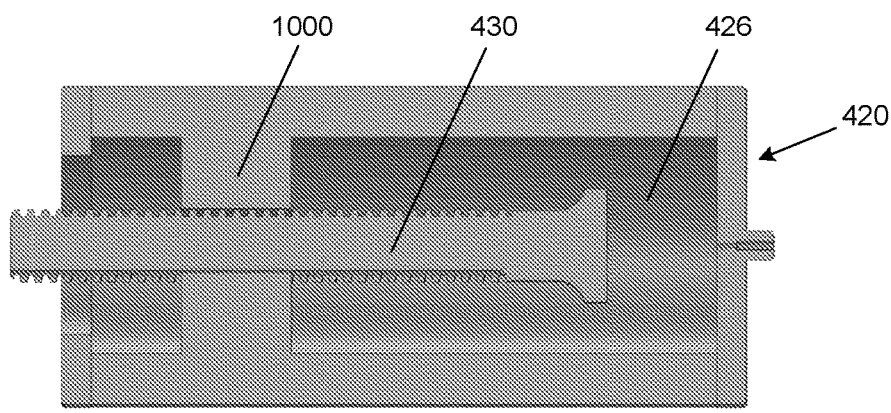
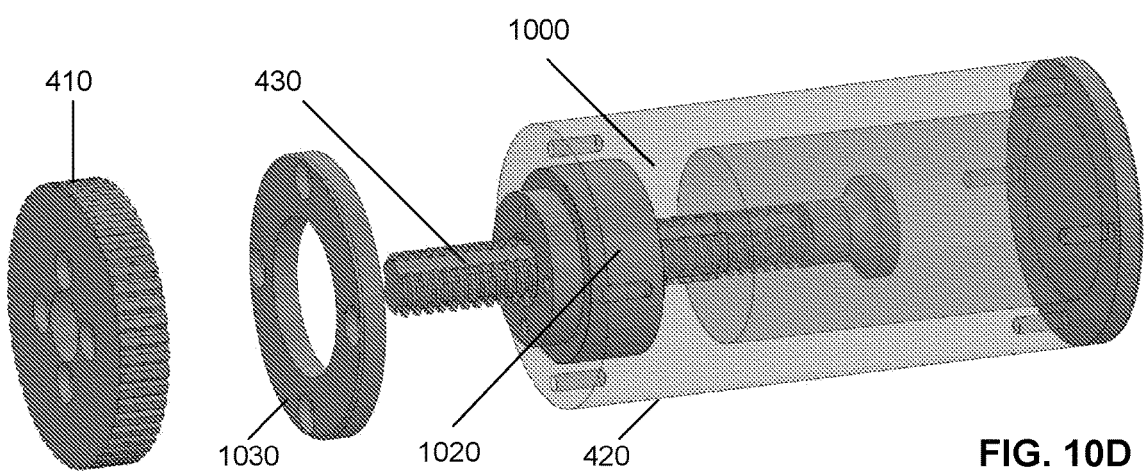

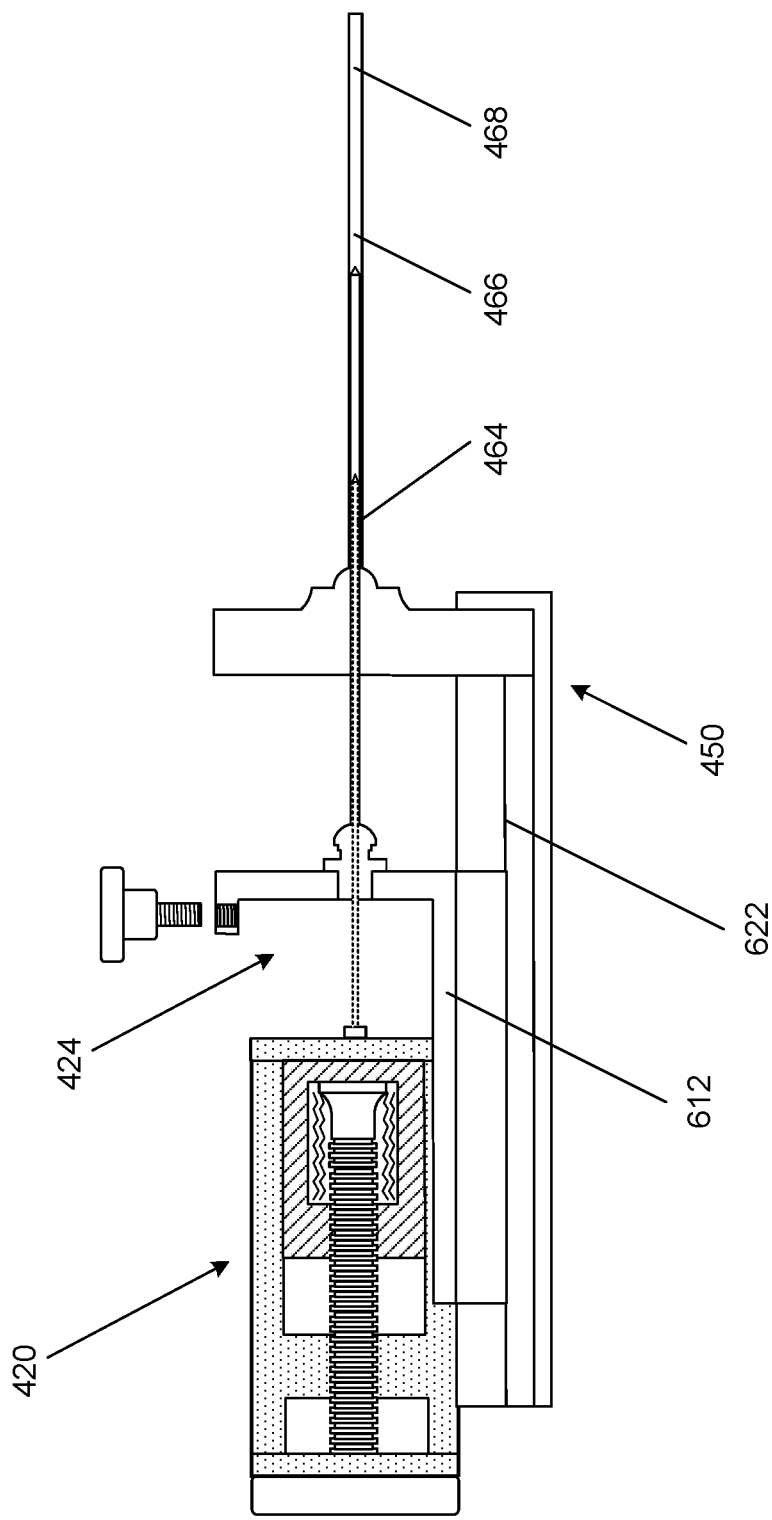

STEERABLE GUIDE FOR MINIMALLY INVASIVE SURGERY

CROSS-REFERENCE TO RELATED APPLICATIONS

This application claims priority to U.S. Provisional Patent App. No. 62/856,487, filed on Jun. 3, 2019, which is hereby incorporated herein by reference as if set forth in full.

BACKGROUND

Field of the Invention

The embodiments described herein are generally directed to a steerable guide for minimally invasive surgery, and, more particularly, to a steerable guide for laser interstitial thermal therapy (LITT) of irregular targets.

Description of the Related Art

Magnetic resonance imaging (MRI) guided LITT has emerged as a safe and effective treatment option for epilepsy and brain tumors that are treatment-refractory or located in deep or eloquent brain. Examples of such treatment are discussed in "Laser Interstitial Thermal Therapy for Mesial Temporal Lobe Epilepsy," Wicks et al., Neurosurgery, vol. 79 supp. 1, pp. S83-S91, December 2016, "Use of a Mobile Intraoperative Computed Tomography Scanner for Navigation Registration During Laser Interstitial Thermal Therapy of Brain Tumors," Jermakowicz et al., World Neurosurg, vol. 94, pp. 418-425, October 2016, "The role of magnetic resonance-guided laser ablation in neurooncology," Banerjee et al., Br J Neurosurg, vol. 29, pp. 192-6, April 2015, and "The impact of stereotactic laser ablation at a typical epilepsy center," Petito et al., Epilepsy Behav, vol. 78, pp. 37-44, January 2018, which are all hereby incorporated herein by reference as if set forth in full.

LITT is capable of generating precise ablative lesions under real-time MM thermometry, while avoiding the morbidity typically associated with open neurosurgical procedures. Currently, to perform this minimally-invasive surgery, a straight catheter is placed within the brain, to serve as a guide for a fiber optic cable that delivers laser light to generate the heat for thermal ablation. Using stereotactic navigation, users plan a linear trajectory, between the extracranial space (e.g., via a craniostomy/dural opening) and the lesion volume, that maximizes lesion coverage while avoiding critical structures. Concurrent real-time MM thermometry allows the user to visualize the ablation zone (e.g., >40° C.) for safe boundaries, while ensuring complete ablation of the lesions.

While this design is minimally-invasive, it has at least the following limitations, due to its linear trajectory:

Ablation of irregular shaped lesions. Primary brain tumors are often very irregular in shape. This makes it challenging to determine a single linear trajectory that completely ablates the lesion. If the lesion is unable to be covered by a single trajectory, the user may need to plan multiple trajectories or consider alternative interventions. This necessarily increases the procedural time, as well as risk to the patient.

Lesions with limited access. Access to lesions is often limited due to surrounding critical structures. This is illustrated by various reports of hemorrhaging or permanent neurological deficits following LITT. See, e.g., "Complication avoidance in laser interstitial thermal therapy: lessons learned," Pruitt et al., J Neurosurg, vol. 126, pp. 1238-45, April 2017, which is hereby incorporated herein by reference as if set forth in full. Consequently, the probe may have to be placed in a suboptimal path to minimize the risk of such complications. This can lead to incomplete ablation and/or unnecessary ablation of healthy tissue.

Lack of touch-up function for incomplete ablations. Currently, it is difficult to preoperatively predict how tissues will respond to thermal energy. Thus, the actual, resulting ablation volume may differ from the planned ablation volume. In some cases, a submaximal lesion may be created, requiring the surgeon to decide if additional laser trajectory placements are needed. While additional placements would require significant added time and endanger healthy tissue, thereby increasing surgical risk, accepting subtotal ablation could mitigate the clinical benefits of the procedure. See, e.g., "Laser thermal ablation for mesiotemporal epilepsy: Analysis of ablation volumes and trajectories," Jermakowicz et al., Epilepsia, vol. 58, pp. 801-810, May 2017, which is hereby incorporated herein by reference as if set forth in full.

SUMMARY

Accordingly, a steerable guide for visualase MRI-guided LITT is disclosed. In an embodiment, the steerable guide comprises: a needle comprising a wire tube and a wire within the wire tube, wherein the wire is fixed to a tip of the needle so as to curve the needle when retracted relative to the wire tube; a shaft with a proximal end and a distal end, wherein the shaft comprises a shaft cavity, and wherein the wire tube is connected to the distal end of the shaft; a spring housing with a proximal end and a distal end, wherein the spring housing is within the shaft cavity, wherein the spring housing comprises a spring cavity and a spring within the spring cavity, and wherein the wire is connected to the distal end of the spring housing; and a translational screw extending through the proximal end of the shaft into the shaft cavity and through a proximal end of the spring housing into the spring cavity, such that a distal end of the translational screw is within the spring cavity, wherein the translational screw is configured to move in each of a proximal direction and a distal direction along a longitudinal axis of the shaft; wherein the spring is positioned, within the spring cavity, between the proximal end of the spring housing and the distal end of the translational screw, such that, when the translational screw moves in the proximal direction while a position of the spring housing is fixed, the spring is compressed between the proximal end of the spring housing and the distal end of the translational screw. The steerable guide may further comprise a knob, attached to the shaft and configured to rotate around the translational screw in each of two rotational directions around the longitudinal axis so as to actuate movement of the translational screw in both the proximal direction and the distal direction.

The wire and/or wire tube may comprise nitinol. The wire tube may comprise one or more notches in at least one side of the wire tube, wherein the one or more notches compress or elongate in response to movement of the wire. The one or more notches may comprise at least nine notches. The spring may comprise thermoplastic polyurethane.

The steerable guide may further comprise an outer sheath releasably fixed to a distal end of a shaft cap and configured to receive the needle through its proximal end, wherein the shaft cap is configured to attach to the distal end of the shaft.

The shaft cap may be configured to releasably attach to the distal end of the shaft. The outer sheath may be closed at its distal end. An outer diameter of the outer sheath may be less than 1.1 millimeters. The outer sheath may comprise ethyl vinyl acetate. The outer sheath may be releasably fixed to the distal end of the shaft cap indirectly by being fixed to a tube holder that is releasably fixed to the distal end of the shaft cap. The steerable guide may further comprise a plunger control configured to receive the shaft cap, such that the shaft cap is capable of sliding relative to the plunger control in both the proximal direction and the distal direction. The steerable guide may further comprise a rigid outer tube connected to a distal end of the plunger control, wherein the rigid outer tube is configured to receive the outer sheath through its proximal end, and wherein the outer sheath is longer than the rigid outer tube, such that, when the shaft cap is slid in the proximal direction relative to the plunger control, the outer sheath is retracted into the rigid outer tube, and, when the shaft is slid in the distal direction relative to the plunger control, the outer sheath is extended out of a distal end of the rigid outer tube. An outer diameter of the rigid outer tube may be less than 2.5 millimeters. The rigid outer tube may comprise nonferrous stainless steel.

The translational screw may comprise one or more longitudinal grooves that extend parallel to the longitudinal axis of the shaft, wherein the shaft comprises a holding portion on a proximal end of the shaft cavity, and wherein the holding portion comprises a through hole with one or more protrusions that are configured to fit within the one or more longitudinal grooves, so as to prevent the translational screw from rotating relative to the shaft.

In an embodiment, a method of operating the steerable guide is disclosed. The method may comprise: while the outer sheath is fully retracted into the rigid outer tube with the needle positioned within the outer sheath, actuating the translational screw to move the translational screw in the proximal direction, so as to at least partially compress the spring, according to a planned curvature amount; moving the shaft cap with the shaft, in the distal direction relative to the plunger control, so as to extend the outer sheath, with the needle positioned within the outer sheath, out of the rigid outer tube, such that the spring decompresses in the proximal direction, thereby pushing the spring housing in the proximal direction relative to the shaft cavity, thereby retracting the wire in the proximal direction relative to the shaft cavity, thereby causing the needle to curve to the planned curvature amount, thereby causing the outer sheath around the needle to curve to the planned curvature amount. The method may further comprise: continuing to move the shaft cap with the shaft in the distal direction until a distal tip of the outer sheath is at a target position; retracting the shaft, so as to retract the needle from the outer sheath, while the shaft cap remains in place; inserting a fiber optic cable into the outer sheath, such that a distal tip of the fiber optic cable is positioned at the distal tip of the outer sheath; and performing ablation at the target position via the fiber optic cable, while running coolant through the outer sheath. A spring constant of the spring may be set such that the needle gradually curves to the predetermined curvature amount as the needle is extended out of the rigid outer tube.

BRIEF DESCRIPTION OF THE DRAWINGS

The details of the present invention, both as to its structure and operation, may be gleaned in part by study of the accompanying drawings, in which like reference numerals refer to like parts, and in which:

FIG. 6C illustrates a shaft of a steerable guide, according to an embodiment;

FIGS. 7A-7C illustrate transparent, side views of the primary components of a steerable guide, disassembled, partially assembled, and fully assembled, respectively, according to an embodiment;

FIGS. 9A-9C illustrate a front view, transparent front view at a first depth, and a transparent front view at a second, deeper depth, respectively, of a steerable guide, according to an embodiment;

FIGS. 10A-10D illustrate a mechanism for translating a screw using a knob, according to an embodiment; and FIGS. 11A-11H illustrate an operation of a steerable guide, according to an embodiment.

DETAILED DESCRIPTION

A steerable guide for LITT is disclosed. For example, the guide may be used with an MRI-guided Visualase™ system, produced by Medtronic PLC, headquartered in Dublin, Ireland. The guide can be especially useful for the treatment of irregular targets (e.g., irregularly shaped brain lesions).

After reading this description, it will become apparent to one skilled in the art how to implement the invention in various alternative embodiments and alternative applications. However, although various embodiments of the present invention will be described herein, it is understood that these embodiments are presented by way of example and illustration only, and not limitation. As such, this detailed description of various embodiments should not be construed to limit the scope or breadth of the present invention as set forth in the appended claims.

Figure 1:
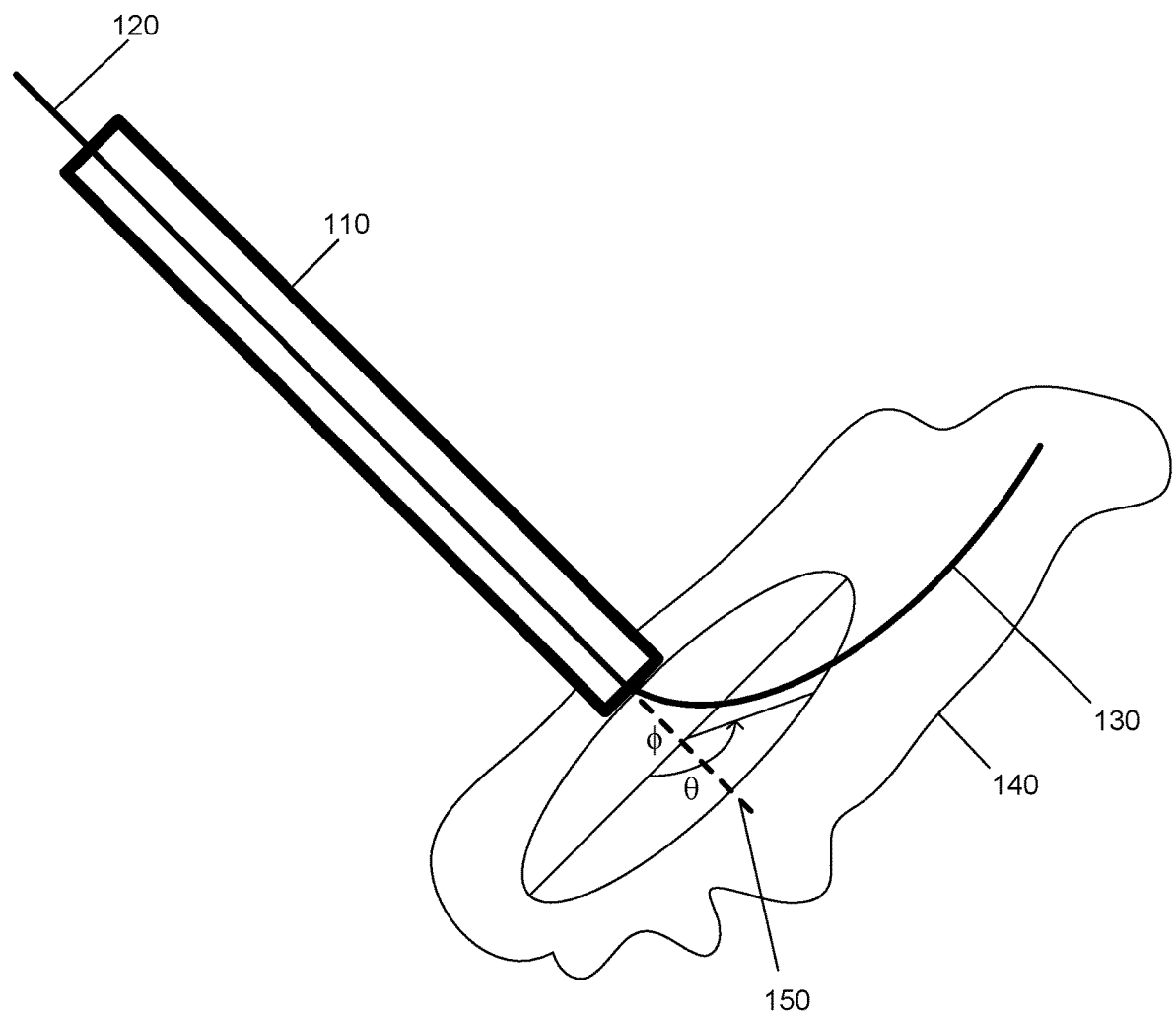
FIG. 1 illustrates the path of a stylet within a tumor, according to an embodiment.

In an embodiment, the steerable guide enables deployment of a laser fiber along a controlled curved trajectory with micro-adjustability, for example, to overcome the shortcomings of the linear guides discussed above. As illustrated in FIG. 1, the guide may comprise or be used with a rigid external cannula 110, surrounding a LITT applicator catheter with a working channel 120 for a laser system, and a steerable stylet 130 (e.g., configured to deliver a laser probe, comprising an optic fiber cable or laser fiber), within the catheter, that allows controlled curved-trajectory deployment beyond cannula 110 into irregular tumor 140, along a specified radial direction or azimuth angle ($\theta$) and a curvature trajectory or angle ($\phi$). Dotted line 150 in FIG. 1 represents an example of the linear trajectory to which current LITT systems are limited, in contrast to the curved trajectory of stylet 130 that may be achieved with the disclosed system. In an embodiment, the azimuth angle (θ) and the curvature angle (φ) of stylet 130 may be controlled to deliver an optic fiber cable to a site within irregular tumor 140 to perform ablation of irregular tumor 140. Such a system may provide at least the following benefits over existing systems:

Achievement of a greater total ablation volume with multiple curved paths from a single rigid cannula placement.

Access to tumors that are currently unreachable through a single access hole. This may expand feasible treatment regions and enhance the surgeon's chances of ablating the entire tumor.

Quick touch-up without increasing the risk of complications in case of incomplete ablation.

Micro adjustments to the curvature angle (φ) in the event of deviations from the planned trajectory caused by needle deflection or tissue deformation.

Figure 2:
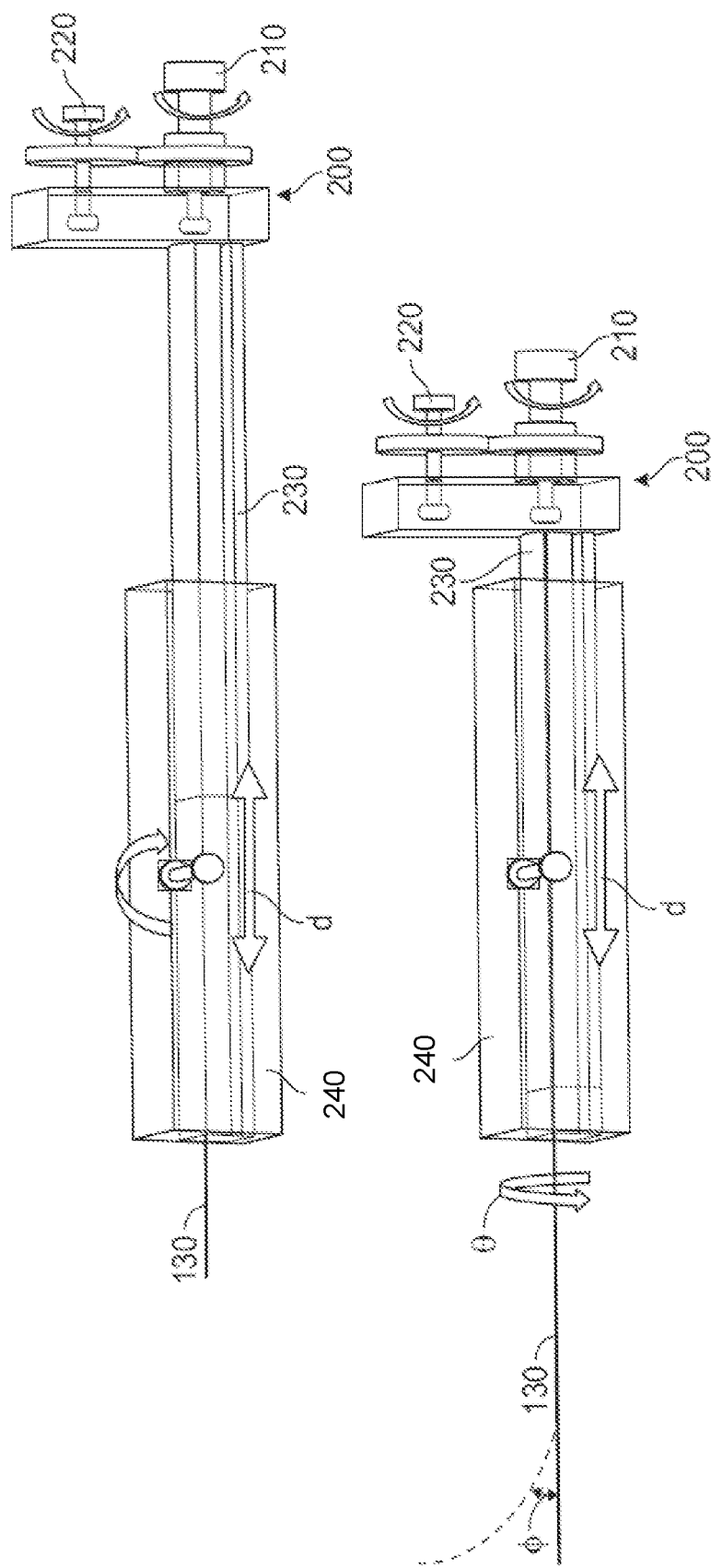
FIG. 2 illustrates a semi-transparent view of a steerable guide, according to an embodiment.

An objective of the steerable guide is to enhance the dexterity of existing straight laser probes, such that tumors with complex geometries, large volumes, and/or multiple local locations can be treated. FIG. 2 illustrates an example of steerable guide, according to an embodiment. In the illustrated embodiment, steerable guide 200 provides three dimensions of freedom (DOF): translation (d), azimuth angle (θ) (also referred to herein as "rotation" or "radial direction"), and curvature angle (φ) (also referred to herein as a curvature "trajectory" or "amount") of stylet 130. Each DOF can be controlled by a manual knob or an MRI-compatible actuator. For example, the curvature angle (φ) may be controlled by knob 210, and the azimuth angle (θ) may be controlled by knob 220.

A rigid cannula is placed in the patient, and an applicator catheter is inserted into the rigid cannula, along a straight path up to the point where the desired curved path should start. A manually controlled steerable stylet 130 that allows a curved deployment is placed within the catheter. Stylet 130 is used to deploy a laser probe beyond cannula 110 (e.g., by carrying a fiber optic cable or carrying a needle that is subsequently replaced by a fiber optic cable), along a specified radial direction (θ) and curvature trajectory (φ). As illustrated in FIG. 2, stylet 130 may be translated using a rack and pinion system comprising a rail 230 that moves within a track 240.

In an embodiment, stylet 130 may comprise an outer sheath. For insertion of stylet 130, a rigid needle is placed within the outer sheath, to guide the tip of the outer sheath to the target destination within tumor 140. Once the tip of the outer sheath is in place, the needle is removed, and an optic fiber cable is inserted into the outer sheath. Ablation can then be performed using the optic fiber cable, while coolant is run through the outer sheath. An example of this embodiment of stylet 130 is disclosed in U.S. Pat. No. 7,270,656, issued on Sep. 18, 2007, which is hereby incorporated herein by reference as if set forth in full. An advantage of this embodiment of stylet 130 is that insertion and removal of the needle, followed by insertion of the optic fiber cable, allows the outer sheath to have a smaller diameter than a stylet which simultaneously contains both the needle and the optic fiber cable.

The curvature trajectory (φ) may be achieved using a tendon-driven mechanism. Specifically, the rigid needle of stylet 130 may comprise one or more notches (e.g., nine notches) towards its distal tip, and one or more tendons that run along the length of the needle and is attached to or near the distal tip of the needle. A handle at the base of the needle is used to pull one of the tendons, thereby increasing the tension, and causing the needle to compress or elongate at the notches, depending on the attachment position of the tendon. The tension applied by the tendon controls the amount of curvature in the needle. An example embodiment of such a needle is disclosed in U.S. Pat. No. 9,161,809, issued on Oct. 20, 2015, which is hereby incorporated herein by reference as if set forth in full.

In an embodiment, the needle may comprise a tube, which may be a nitinol tube, and at least one tendon, which may be a nitinol wire. Nitinol is a biocompatible, nickel-titanium alloy that has elastic properties. The nitinol wire may run from one end of the nitinol tube, through the nitinol tube, to the other end of the nitinol tube, and be staked to the closed distal tip of the nitinol tube. The nitinol tube may comprise one or more notches near the distal tip to allow a controlled buckling of the nitinol tube when the nitinol wire is pulled to apply tension to the tip of the nitinol tube. The maximum or range of curvature of the needle may be set to an appropriate amount by varying the length of the notch(es) and/or the number of notches. In an embodiment, the needle comprises at least nine notches, which are each around 3 mm in length, with a distance between notches of around 1.88 mm. In one implementation, the total length of the nitinol tube is 265 mm, and the total length of the wire is 270 mm.

In an embodiment, steerable guide 200 has one or more of the following features:

Steerable guide 200 deploys stylet 130 along a curved trajectory, as opposed to first deploying the stylet along a straight line and then curving the stylet at the tip. This latter method would cause a sweeping motion that can cut through surrounding tissue, which may cause damage or deformation of healthy tissue and/or critical structures.

Figure 3:
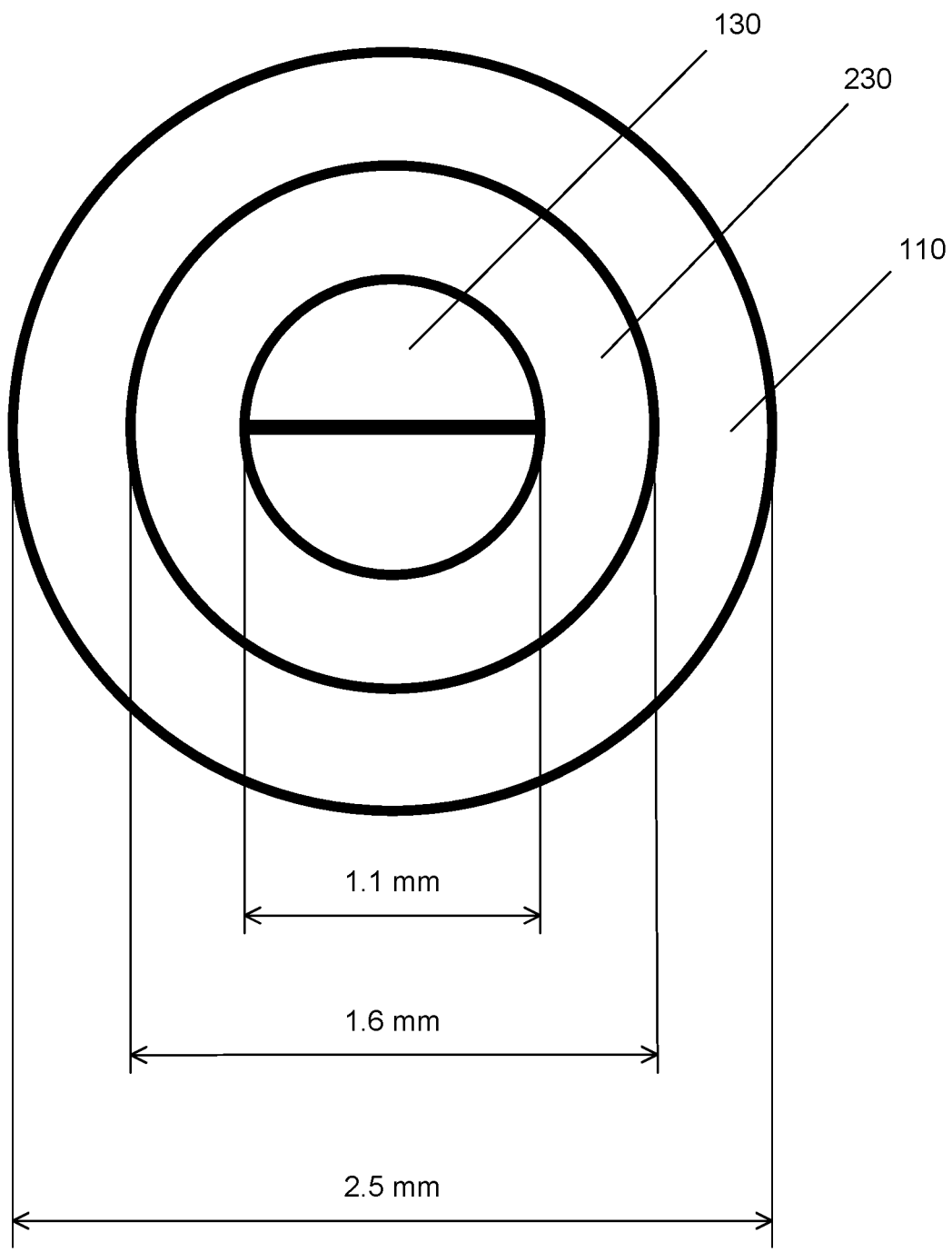
FIG. 3 illustrates exemplary cross-sectional diameters of components used by a steerable guide, according to an embodiment.

Steerable guide 200 integrates with existing LITT systems and surgical work-flows. In this case, the outer diameter of steerable stylet 130 should be less than 1.1 mm, the diameter of catheter 230 should be between 1.1 mm and 1.6 mm, and the inner and outer diameters of rigid cannula 110 should be 1.6 mm and 2.5 mm, respectively, as illustrated in FIG. 3, according to an embodiment.

Steerable guide 200 should be MRI-compatible and not affect thermometry compatibility.

Steerable guide 200 should be disposable or sterilizable, and rigid cannula 110 must be biocompatible.

Several mechanisms have been developed to control the curvature of needle-like devices, including catheters, steerable needles, and steerable cannulas. However, none of the existing designs have all the features listed above. The following is a brief summary of existing designs for steering needle-like devices, as well as their limitations for LITT:

The beveled-tip mechanism utilizes the asymmetric tissue reaction force on a beveled tip of a flexible needle to steer the needle. An example of this mechanism is described in "Teleoperation of steerable needles," Romano et al., Proceedings of the 2007 IEEE Int'l Conference on Robotics and Automation, vols. 1-10, pp. 934-9, 2007, which is hereby incorporated herein by reference as if set forth in full. For this mechanism, a flexible needle is rotated while being inserted to control the direction of the reaction force, and ultimately its curvature. However, this approach requires modifying the applicator catheter to have a beveled tip. In addition, the beveled tip makes it difficult to insert the catheter along a straight path. Moreover, the combined stiffness of the catheter and inner stylet may be too rigid, which limits the maximum achievable curvature.

The push-pull mechanism curves the tip of the needle by applying a compression or tension force on one side of a hollow needle. An example of this mechanism is described in U.S. Patent Pub. No. 2012/0136381, published on May 31, 2012, which is hereby incorporated herein by reference as if set forth in full. Typically, there is at least one notch on one side of the needle, so that compression or elongation can occur on that side. Since the brain is a soft and spongy tissue, this mechanism has the benefit that it does not rely upon tissue interaction forces. In addition, micro adjustments may be performed in the event that slight deviations from the planned trajectory occur. However, these needles are used by initially inserting them along a straight trajectory, then curving them to reach the target. Since this sweeping motion cuts through the surrounding tissue, it should be avoided for LITT, as it may cause damage or deformation to non-target tissue.

Another mechanism involves deploying a pre-curved needle out of a rigid outer tube to achieve curved paths. An example of this mechanism is described in "Handheld steerable needle device," Okazawa et al., IEEE/ASME Transactions on Mechatronics, vol. 10, pp. 285-96, June 2005, which is hereby incorporated herein by reference as if set forth in full. For this mechanism, a pre-curved nitinol wire is generally used, due to its characteristics of being super-elastic, yet stiff enough to be pushed without causing significant lateral deflection or buckling. See, e.g., "Nitinol medical device design considerations," Poncet, 2003, which is hereby incorporated herein by reference as if set forth in full. While this mechanism allows a curvature to be achieved, without damaging the surrounding tissue due to a sweeping motion (e.g., as in the push-pull mechanism), the needle is limited to a single curvature trajectory. Also, the needle lacks the capability to be adjusted for deviations from the planned trajectory.

In an embodiment, steerable guide 200 overcomes the shortcomings in these current mechanisms. Specifically, a needle that can be curved using the push-pull mechanism is placed within catheter 230, which is then placed in rigid cannula 110, as illustrated in FIG. 3. The curvature amount of the needle is controlled by the tension induced by the push-pull mechanism (e.g., using a nitinol wire), while the needle is within a rigid outer tube. Thus, when the tensioned needle is pushed out of the rigid outer tube, it acts as a pre-curved needle that follows a curved path without a sweeping motion, so as to avoid damaging the surrounding healthy tissue.

When the needle is within the rigid outer tube, the rigid outer tube suppresses the needle from being curved as the tension is applied by the wire. As the tension increases (e.g., to produce a larger curvature angle), the friction between the curved needle and rigid outer tube increases, thereby making it difficult to push the curved needle out of the rigid outer tube. Also, when the tension exceeds a certain limit, the connection between the wire and the needle may break, leading to a failure of the curved needle. To achieve a curvature that exceeds this limit, the user would have to simultaneously control the applied tension amount as the curved needle is being pushed out of the rigid outer tube. However, a repeatable trajectory would be hard to achieve using this method. Moreover, there is the risk of a sudden change in the tension amount, which could cause a sweeping motion, resulting in unintended tissue damage.

Figure 4A:
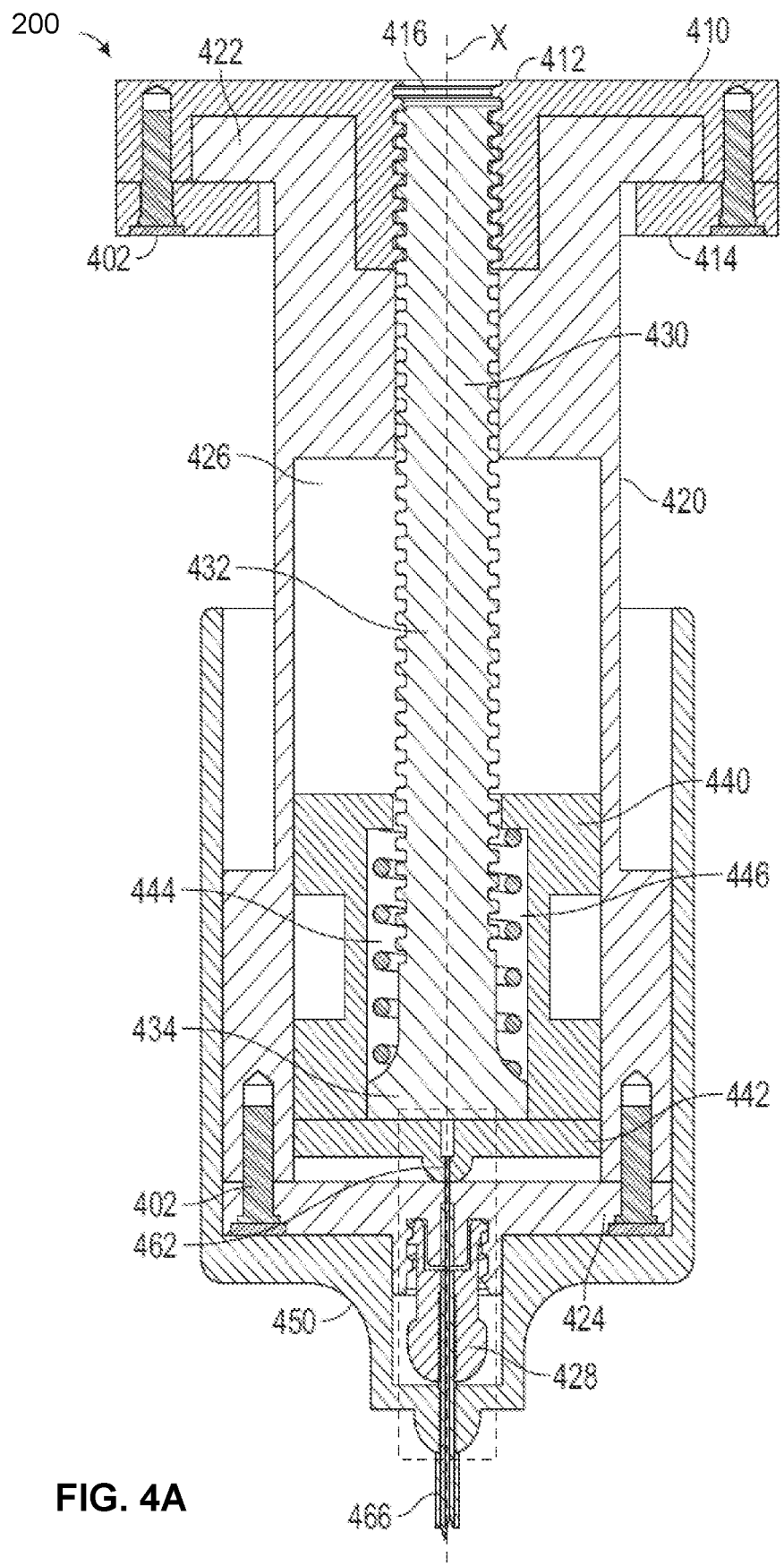
FIGS. 4A and 4B illustrate a cross-sectional view of a housing of the steerable guide, according to an embodiment.
Figure 4B:
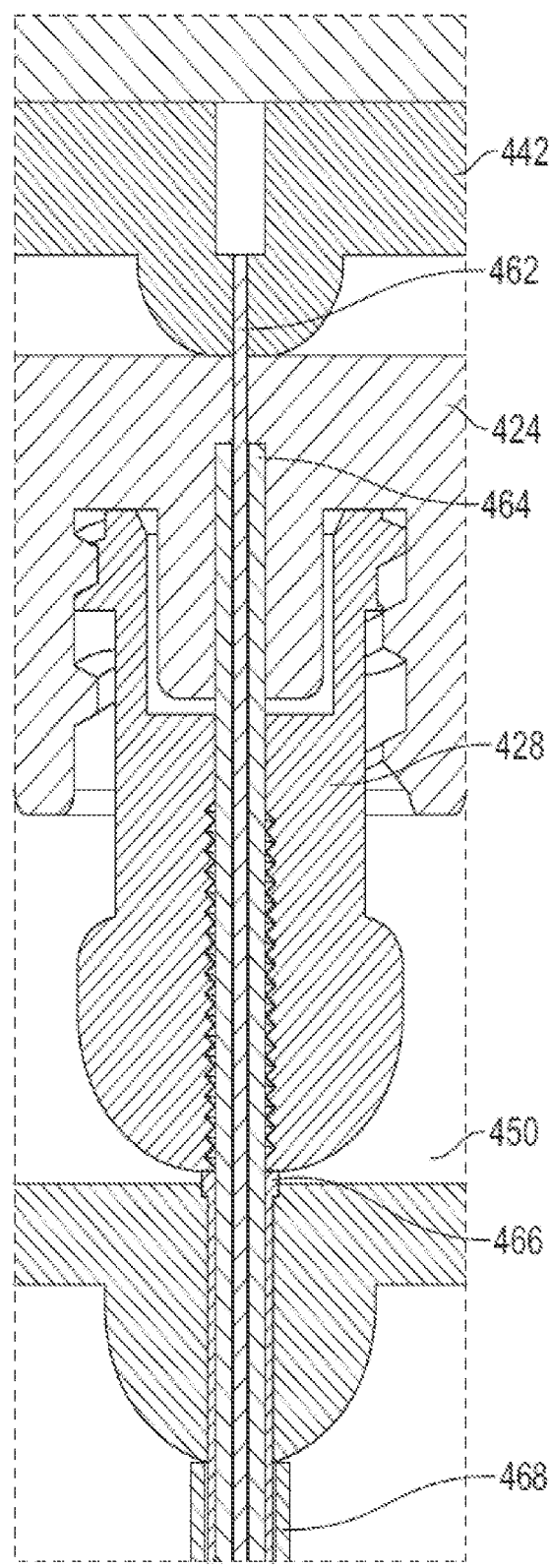

Thus, in an embodiment, a spring housing is added to overcome this limitation. FIG. 4A illustrates components of steerable guide 200, according to such an embodiment. FIG. 4B illustrates a close-up view of the region enclosed by the dashed box in FIG. 4A, according to an embodiment. Steerable guide comprises a knob 410, a shaft 420, a translational screw 430, a spring housing 440, and a plunger control 450. As used herein, the term "proximal" will refer to a position closer to knob 410, along longitudinal axis X, whereas the term "distal" will refer to a position farther from knob 410, in the direction of shaft 420 and plunger control 450, along longitudinal axis X.

Knob 410 may comprise a knob top portion 412 and a knob bottom portion 414. A shaft flange 422 of shaft 420 is disposed and held between knob top portion 412 and knob bottom portion 414. Knob top portion 412 and knob bottom portion 414 may be fastened together using one or more screws 402 and/or any other fastening means. For example, screws 402 may be inserted through holes in the distal surface of knob bottom portion 414 and threaded into corresponding threaded holes in knob top portion 412 to thereby seal knob bottom portion 414 to knob top portion 412. In addition, knob 410 comprises a threaded hole 416 through both the bottom and top surfaces of knob 410.

Threaded hole 416 is configured to mate with a threaded screw body 432 of translational screw 430. As knob 410 is rotated, threaded hole 416 rotates around translational screw 430, guiding the mated threads in threaded screw body 432, so as to change the position of knob 410 relative to translational screw 430, along longitudinal axis X of steerable guide 200. For example, if knob 410 is rotated in one rotational direction (e.g., clockwise or counterclockwise), a flared end 434 of translational screw 430 may move closer to knob 410, as translational screw 430 moves proximally through threaded hole 416. Conversely, if knob 410 is rotated in the opposite rotational direction (e.g., counterclockwise or clockwise), flared end 434 may move farther from knob 410, as translational screw 430 moves distally through threaded hole 416. In addition, if no rotation is applied to knob 410, the positions of knob 410 and translational screw 430 are fixed relative to each other, via the mated threads, such that no translation of translational screw 430 can occur along longitudinal axis X. Thus, translational screw 430 can be fixed at various positions relative to knob 410, along the longitudinal axis X of steerable guide 200.

Knob 410 is coupled to shaft 420 by enclosing shaft flange 422, but is not positionally fixed to shaft flange 422. Thus, knob 410 is capable of rotating around shaft flange 422, without imparting rotation to shaft 420. In addition, shaft 420 may be configured so that it does not rotate as translational screw 430 translates. Translational screw 430 extends, along longitudinal axis X, from threaded hole 416 in knob 410, through a non-threaded hole in the proximal end of shaft 420, into a shaft cavity 426 within shaft 420. In addition, translational screw 430 extends through a non-threaded hole into a spring cavity 444 of spring housing 440, such that flared end 434 of translational screw 430 is positioned within spring cavity 444 of spring housing 440. It should be understood that the range of movement of translational screw 430, along longitudinal axis X, is defined by the length of shaft cavity 426 and the dimensions of the portion of spring housing 440 and a spring 446 between flared end 434 and the proximal end of shaft cavity 426.

Within spring housing 440, spring 446 is positioned between the proximal end of spring cavity 444 and flared end 434 of translational screw 430. Thus, as flared end 434 of translational screw 430 moves, along longitudinal axis X, relative to spring housing 440, it compresses or decompresses spring 446. Specifically, if flared end 434 moves towards the proximal end of spring cavity 444, while the position of spring housing 440 is fixed, flared end 434 compresses spring 446. Conversely, if flared end 434 moves towards the distal end of spring cavity 444 or if the position of spring housing 440 becomes unfixed, spring 446 will decompress by virtue of its spring force. To be MRI-compatible, spring 446 may be manufactured (e.g., 3D-printed) using thermoplastic polyurethane (TPU).

Flared end 434 may also prevent translational screw 430 from fully passing through the non-threaded hole at the proximal end of spring housing 440, thereby ensuring that translational screw 430 and spring housing 440 always remain coupled to each other. Spring housing 440 is configured to slide smoothly within shaft cavity 426, along longitudinal axis X. However, it should be understood that the distance and direction, which spring housing 440 may slide within shaft cavity 426, is limited by translational screw 430 and spring 446, as well as the length of shaft cavity 426. In addition, movement of spring housing 440 is limited by its connection to wire 462, as discussed in further detail below.

Spring housing 440 may comprise a spring housing cap 442 on its distal end. Spring housing cap 442 is fixed to a wire 462 (e.g., a nitinol wire being used as a tendon in a needle). Wire 462 may be permanently fixed to spring housing cap 442 via epoxy or glue. Thus, wire 462 and spring housing 440 are fixed to each other, such that movement of spring housing 440 causes a corresponding movement of wire 462, and fixation of wire 462 causes a corresponding fixation of spring housing 440. Wire 462 may run through a wire tube 464 and be fixed at an attachment point to the distal tip of the needle, defined by wire tube 464. Thus, retraction of wire 462 pulls the tip of the needle, causing the needle to curve, for example, by virtue of one or more notches in wire tube 464 (e.g., a nitinol tube).

Shaft 420 may comprise a shaft cap 424 on its distal end. Shaft cap 424 may be fixed to a main body of shaft 420 by one or more screws 402 and/or other fastening means. For example, screws 402 may be inserted through holes in a distal surface of shaft cap 424 and threaded into corresponding threaded holes in the main body of shaft 420, to thereby seal shaft 424 to the main body of shaft 420. Wire tube 464 is fixed to a hole in the center of shaft cap 424, and may be permanently fixed to shaft cap 424 via epoxy or glue.

In addition, shaft cap 424 may be releasably fixed to a tube holder 428 (e.g., the Medtronic Visualase™ catheter). For example, tube holder 428 may comprise one or more threads on an exterior proximal end that are configured to rotationally mate with a threaded hole in the center of shaft cap 424. Thus, tube holder 428 may be screwed into shaft cap 424 to fix tube holder 428 to shaft cap 424, and screwed out of shaft cap 424 to release tube holder 428 from shaft cap 424. The distal end of tube holder 428 is fixed to a plastic tube 466, which is configured to receive the needle (i.e., comprising or consisting of wire tube 464 with wire 462 therein) therein. It should be understood that plastic tube 466 represents the outer sheath of stylet 130. Plastic tube 466 prevents tissue from entering the needle and permits subsequent ablation via removal of the needle and insertion of a fiber optic cable. Plastic tube 466 should fit snugly around wire tube 464, but have enough flexibility that it does not hinder the curvature of the needle. For example, in an embodiment, the diameter of plastic tube 466 is at least 0.432 mm wider than the outer diameter of wire tube 464. Plastic tube 466 may be permanently fixed (e.g., by epoxy or glue) or releasably fixed (e.g., via mating threads) to tube holder 428.

In an embodiment in which tube holder 428 is releasably fixed to shaft cap 424, tube holder 428 may be released from shaft cap and replaced by a new tube holder 428 with another plastic tube 466. In this manner, the outer sheath of stylet 130 may be easily replaced. In addition, in an embodiment, the needle may also be replaced by unscrewing and replacing shaft cap 424 and spring housing cap 442 with a shaft cap 424 and spring housing cap 442 that are fixed to a new needle. Thus, the needle can also be replaced.

Shaft 420 is configured to fit snugly into and slide within plunger control 450, along longitudinal axis X. In other words, the entire assembly comprising shaft 420—with knob 410 on the proximal end, the needle on the distal end, and spring housing 440 inside—is configured to move within plunger control 450 along longitudinal axis X. A rigid outer tube 468 is attached to a distal exterior surface of plunger control 450, and is configured to receive plastic tube 466 therein.

Rigid outer tube 468 is configured to keep stylet 130 straight as it enters the patient. The needle is made of flexible material, which cannot be kept straight without a rigid backbone. Thus, rigid outer tube 468 acts as such a backbone. In an embodiment, rigid outer tube 468 comprises a nonferrous 316 stainless steel or nitinol. The inner diameter of rigid outer tube 468 should be sized to allow plastic tube 466 to slide through it with little friction. For example, the inner diameter of rigid outer tube 468 may be at least 0.381 mm wider than the outer diameter of plastic tube 466.

The table below illustrates some exemplary, non-limiting materials and dimensions of wire 462, wire tube 464, plastic tube 466, and rigid outer tube 468, according to an embodiment:

|  | Wire 462 | Wire Tube 464 | Plastic Tube 466 | Outer Tube 468 |
| --- | --- | --- | --- | --- |
| Material | Nitinol | Nitinol | Ethyl Vinyl Acetate | Stainless Steel |
| Inner Diameter (mm) | — | 0.33 | 1.016 | 2.159 |
| Outer Diameter (mm) | 0.3048 | 0.584 | 1.778 | 2.413 |

Translation of stylet 130 (i.e., comprising plastic tube 466, potentially with the needle therein), is controlled by a plunger mechanism (or rack and pinion mechanism). Specifically, plunger control 450 acts as a guide for the translation. Shaft 420, which is coupled to the stylet by virtue of its direct connections to plastic tube 466 and wire tube 464 and its indirect connection to wire 462 via spring housing 440, slides within plunger control 450 to move plastic tube 466, with the needle therein, within rigid outer tube 468. The curvature angle ($\phi$) of the needle, and thereby stylet 130, is controlled by the screw-spline mechanism, which comprises the relative translation between knob 410 and translation screw 430, caused by rotation of knob 410. Rotational movement of the needle, and thereby stylet 130, may be controlled by holding or rotating shaft 420 as needed (or as knob control 220). Thus, steerable guide 200 provides movement in at least three dimensions of freedom.

Figure 5:
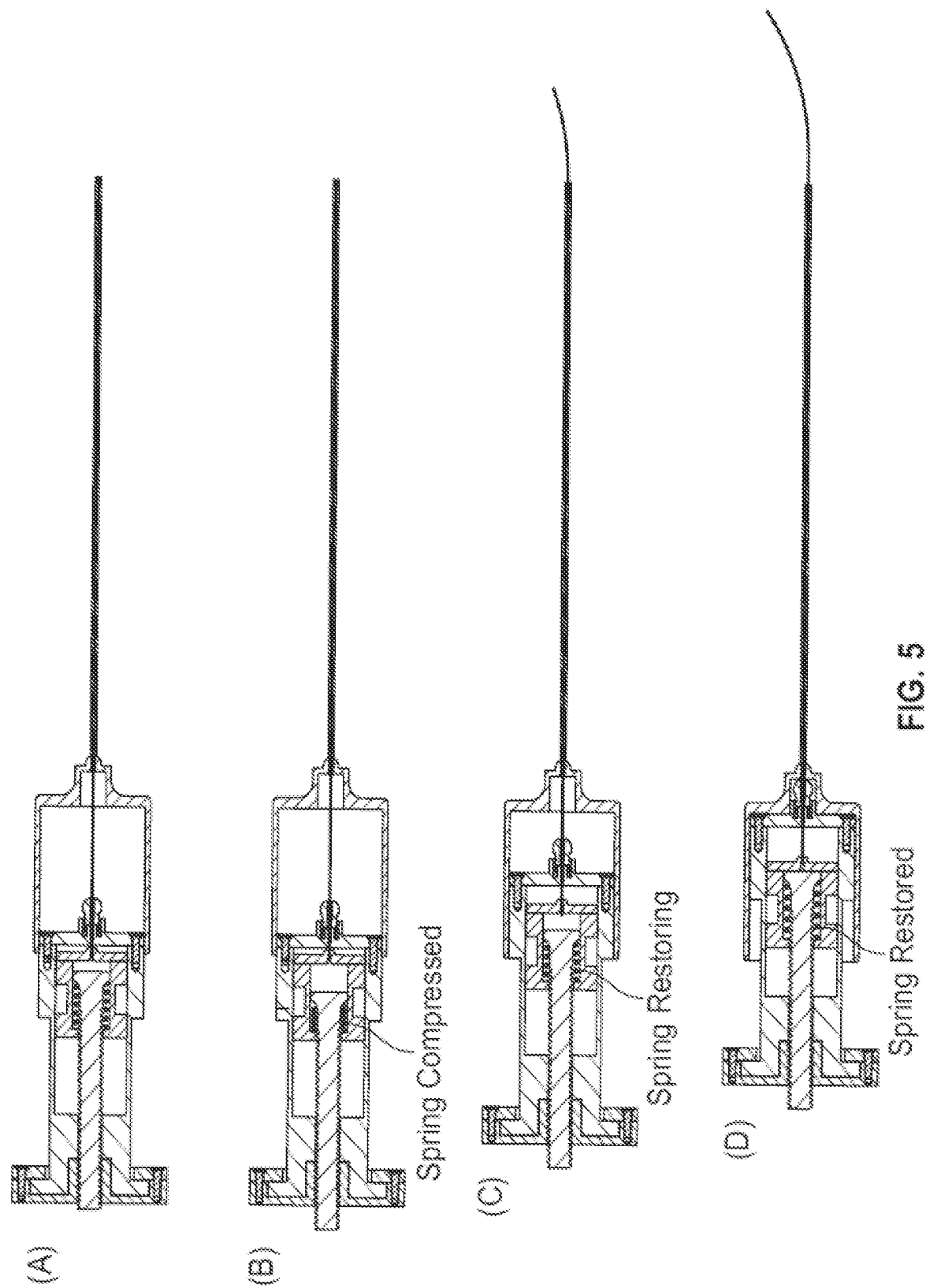
FIG. 5 illustrates an operation of the housing of the steerable guide illustrated in FIGS. 4A and 4B, according to an embodiment.

FIG. 5 illustrates operation of spring housing 440 from FIG. 4A, according to an embodiment. For this illustration, it is assumed that the insertion point (not shown) has been properly prepped, and that the plunger control 450 from FIG. 4A has been previously positioned with respect to the patient. For example, the patient's head may be completely anesthetized and registered with the navigation system for an ablation procedure. Once the trajectory has been chosen, a hole is burred into the patient's head and a bone anchor is placed into the skull. Plunger control 450 may be positioned with rigid outer tube 468 inserted into the hole in the patient's head along the planned trajectory to tumor 140. Plunger control 450 and shaft 420 may be fixed to the patient by a stereotactic frame, which offers stability to steerable guide 200, as stylet 130, with the needle therein, is inserted into the patient.

Initially, in step (A), shaft 420 is positioned proximally with respect to plunger control 450, such that stylet 130 does not yet extend from the distal end of rigid outer tube 468. In other words, stylet 130 is positioned such that its distal tip within rigid outer tube 468. Because stylet 130, comprising plastic tube 466 with the needle therein, is attached to the distal end of shaft 420, it moves with shaft 420.

In step (B), knob 410 is rotated to retract translational screw 430 towards and through the proximal end of shaft 420. As flared end 434 of translational screw 430 is retracted, spring 446 is compressed between the proximal end of spring housing 440 and flared end 434 of translational screw 430. Because spring housing cap 442 is fixed to wire 462, spring housing 440 does not move with translational screw 430. Specifically, the needle is still within rigid outer tube 468, and therefore, is incapable of curving. Thus, wire 462 is effectively fixed in place, thereby fixing spring housing 440 in place by virtue of the connection between the two. Consequently, once spring 446 is fully compressed, no further retraction of translation screw 430 is possible.

Effectively, the user is storing the tension that would normally be applied to the needle (i.e., via wire 462) in spring 446. Since the tension is transferred from the needle to spring 446, spring 446 prevents the potential needle failure that would be caused by the needle's inability to curve within rigid outer tube 468. The maximum curvature amount ($\phi$) is represented by a fully compressed spring, the minimum curvature amount ($\phi$) (e.g., no curvature) is represented by a fully uncompressed spring, and the user may set the curvature amount ($\phi$) to anything between these two extremes by proportionally compressing spring 446. In other words, translational screw 430 can be retracted to different positions to allow for different curvature amounts. In this manner, the curvature amount ($\phi$) of the needle is set in advance, prior to stylet 130 exiting rigid outer tube 468.

In addition, in step (B), shaft 420 may be rotated around longitudinal axis X. Since stylet 130 is attached to the distal end of shaft 420, stylet 130, with the needle therein, rotates with shaft 420. Thus, the needle may be rotated about the longitudinal axis X, which is also the insertion axis, to control the radial direction ($\theta$) of stylet 130, while stylet 130 is still within rigid outer tube 468.

In step (C), the user pushes shaft 420 distally into plunger control 450. Since stylet 130 is attached to the distal end of shaft 420, this causes the distal end of stylet 130 to exit rigid outer tube 468. Once the distal end of stylet 130 exits rigid outer tube 468, it is capable of curving in the radial direction ($\theta$) to which the needle was rotated. Specifically, because the needle is now capable of curving, wire 462 is no longer effectively fixed in place. Thus, spring housing 440 is capable of sliding within shaft cavity 426. Because spring housing 440 is now capable of sliding, compressed spring 446 releases its tension. However, translational screw 430 is fixed in place in shaft cavity 426, such that flared end 434 prevents spring 446 from decompressing distally. Consequently, spring 446 is forced to decompress proximally, thereby pushing against the proximal end of spring housing 440, and causing spring housing 440 to slide towards the proximal end of shaft cavity 426.

As illustrated in step (D), spring 446 will fully decompress (e.g., until the distal end of spring housing 440 abuts flared end 434 of translational screw 430). As spring housing 440 moves proximally, due to the proximal decompression of spring 446, wire 462 is retracted by virtue of its attachment to spring housing cap 442. This retraction of wire 462 applies tension to the needle, thereby causing the needle to curve gradually as it exits rigid outer tube 468, in proportion to the amount of tension stored when spring 446 was compressed. In essence, spring 446 transfers its tension to the needle. As stylet 130, with the needle therein, continues to exit rigid outer tube 468, the increase in curvature will continue gradually until the curvature, set in step (B) and stored in spring 446, is reached.

At that point, stylet 130 can be pushed deeper into the brain, following the trajectory determined by the curvature of the needle. This may be done under the guidance of MRI or computerized tomography (CT). Specifically, the user of steerable guide 200 may monitor a display showing the current location of the needle in the patient's brain throughout the entire process.

Once stylet 130 has reached the target position, the needle may be removed, while plastic tube 466 remains in place with its tip at the target position. For example, the needle may be removed by detaching tube holder 428 from shaft cap 424 (e.g., by disengaging the mated threads), using any known fastening mechanism, and retracting detached shaft 420 from plunger control 450. A fiber optic cable is then inserted into plastic tube 466, and the ablation procedure is performed via the fiber optic cable. During ablation at the target position, coolant may be run through plastic tube 466 to prevent ablation of the tissue surrounding plastic tube 466. In addition, plastic tube 466 may be retracted to perform ablation along the curved path.

Notably, the operation in FIG. 5 may be reversed, in order to retract the needle in a manner that prevents damage to healthy tissue. This is possible because spring 446 will compress as the forces of rigid outer tube 468 act on the needle. Specifically, as the needle re-enters rigid outer tube 468, the rigidity of outer tube 468 will force the needle to gradually un-curve back into a linear configuration. This will force the proximal end of wire 462 to move distally towards wire tube 464, thereby pulling spring housing 440 distally and compressing spring 446 against flared end 434 of translational screw 430. Accordingly, the tension in the needle is transferred back into spring 446.

The described operation depicted in FIG. 5 enables a user to store a curvature amount ($\phi$), using spring 446, and delay deployment of the curvature through force properties. The spring constant of spring 446 can be set to an amount that deploys the curvature amount ($\phi$) according to an appropriate rate. If the spring constant is too strong, the tension to wire 462 may cause the needle to deform while it is still within rigid outer tube 468. Conversely, if the spring constant is too weak, the tension to wire 462 may not be sufficient to cause curvature of the needle. In addition, to ensure MRI-compatibility, spring 446 should not be manufactured from ferrous materials.

In an alternative embodiment, spring housing 440 could be omitted. In this case, translational screw 430 could be coupled, either directly or indirectly, to wire 462, such that retraction of translational screw 430 directly causes the needle to curve. However, deployment of the curved needle is more complicated in such an embodiment. In particular, the user would need to utilize step motion, which comprises slight step-wise movements in each DOF. For example, the user may need to perform tedious, repetitive sequences of slight translations (e.g., pushing or pulling shaft 420), rotations (e.g., rotating shaft 420), and curves (e.g., moving translational screw 430 by turning knob 410) until the tip of the needle has reached its target position. Furthermore, these sequences would then need to be reversed to safely remove the needle. Alternatively, instead of manual control, an MRI-compatible automated system could be used to automatically control the step-wise movements, in forward and reverse, using a plurality of actuators (e.g., piezoelectric motors, pneumatic stepper motors, etc.).

Figure 6A:
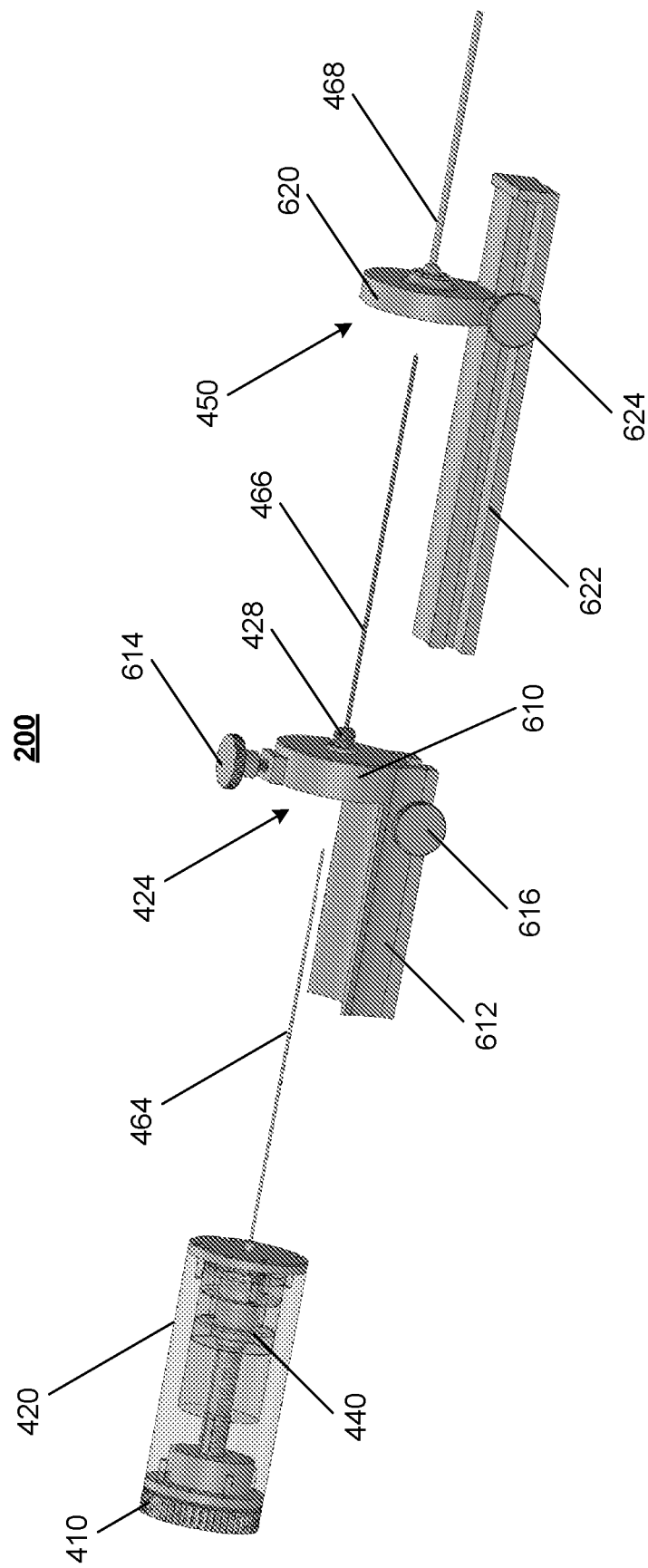
FIGS. 6A and 6B illustrate transparent perspective views of the primary components of a steerable guide, disassembled and assembled, respectively, according to an embodiment.

FIGS. 6A-11H illustrate steerable guide 200, according to an alternative embodiment. Specifically, FIGS. 6A and 6B illustrate transparent perspective views of the primary components of steerable guide 200, disassembled and assembled, respectively, according to an embodiment. FIG. 6C illustrates a cross-sectional view of shaft 420, according to an embodiment. Notably, shaft 420 comprises many of the same elements as described with respect to FIGS. 4A and 4B. FIGS. 7A-7C illustrate transparent, side views of the primary components of the steerable guide 200, disassembled, partially assembled, and fully assembled, respectively, according to an embodiment. FIGS. 8A-8C illustrate transparent, top views of the primary components of the steerable guide 200, disassembled, partially assembled, and fully assembled, respectively, according to an embodiment. FIGS. 9A-9C illustrate a front view, transparent front view at a first depth, and a transparent front view at a second, deeper depth, respectively, of steerable guide 200, according to an embodiment. FIGS. 10A-10D illustrate a transparent front view of knob 410, front perspective view of a holding portion of shaft 420, a cross-sectional view of shaft 420, and an exploded perspective view of knob 410 and shaft 420, respectively, according to an embodiment. FIGS. 11A-11H illustrate an operation of steerable guide 200, according to an embodiment. The alternative embodiment, illustrated in these figures, shares many of the same components as the steerable guide 200 described in FIGS. 4A-5. Thus, in order to avoid repetitiveness, only the differences will be described. Accordingly, any component that is not specifically discussed with respect to FIGS. 6A-11H may be assumed to be similar or identical to the corresponding components described with respect to FIGS. 4A-5.

Figure 6B:
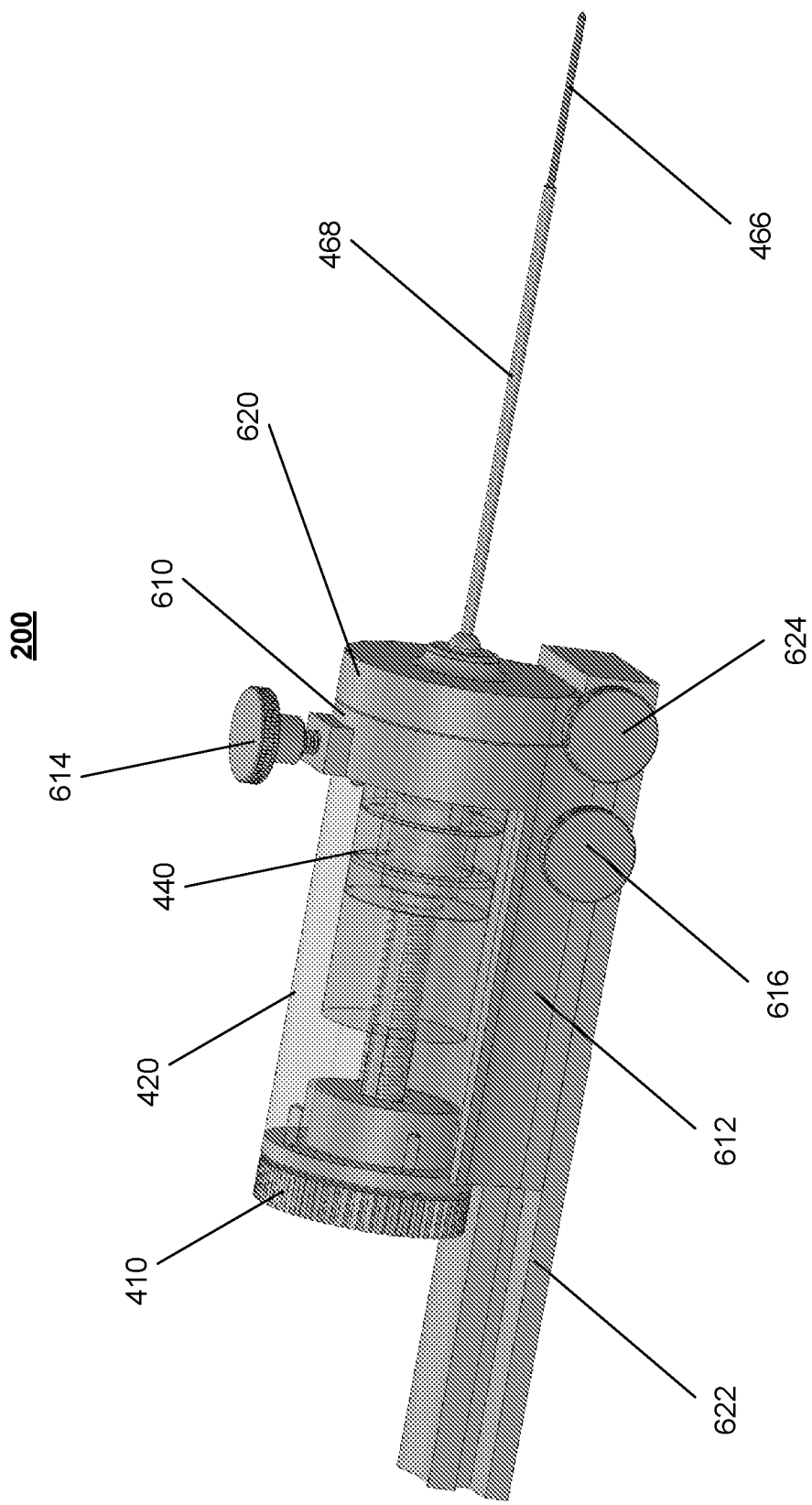
Figure 7A:
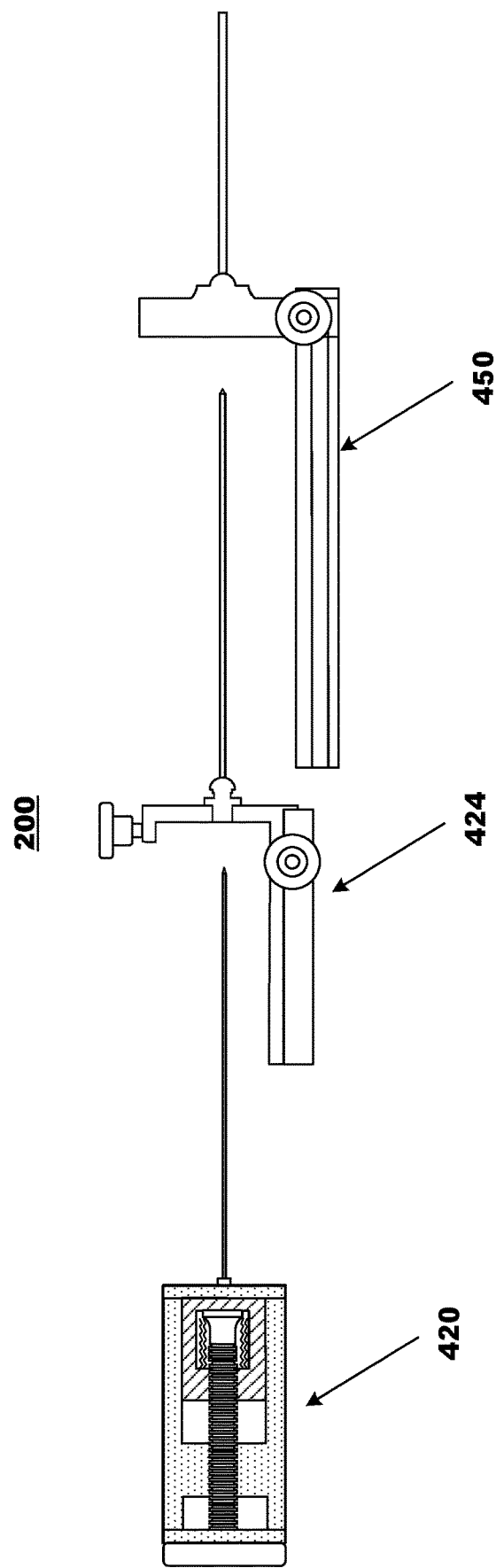
Figure 7B:
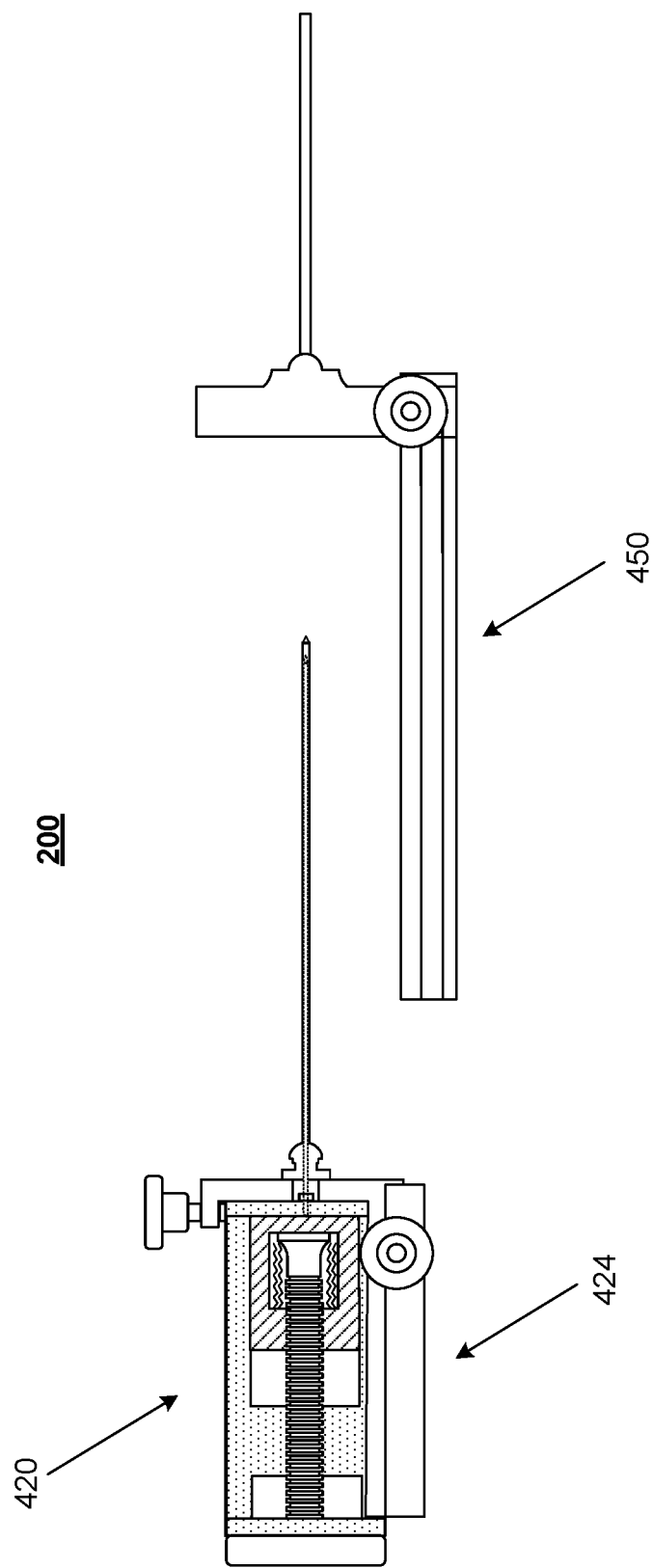
Figure 8A:
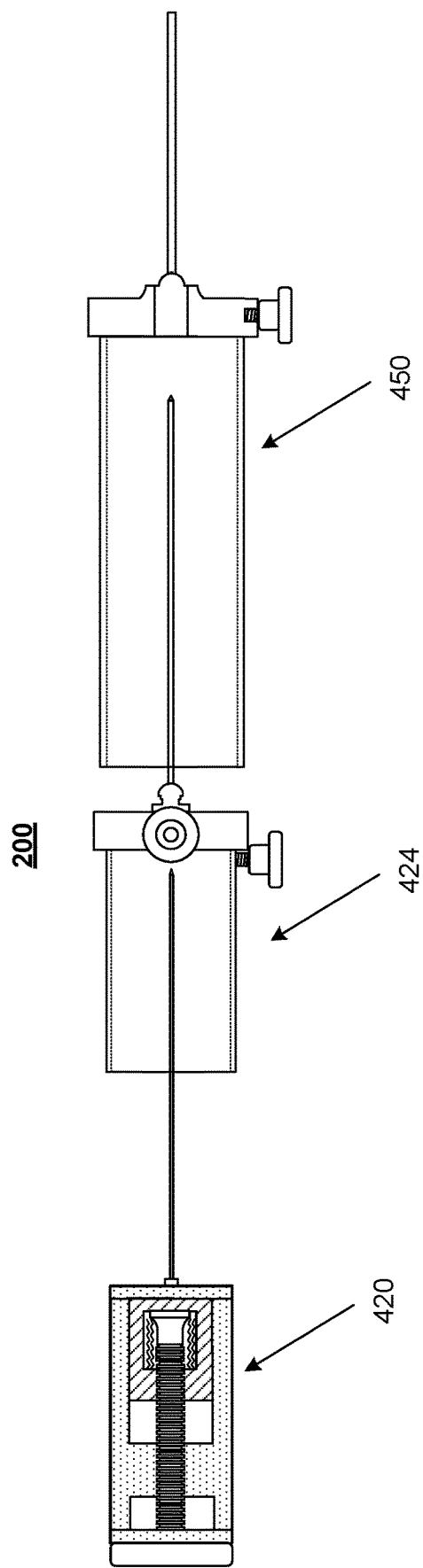
FIGS. 8A-8C illustrate transparent, top views of the primary components of the steerable guide 200, disassembled, partially assembled, and fully assembled, respectively, according to an embodiment.
Figure 8B:
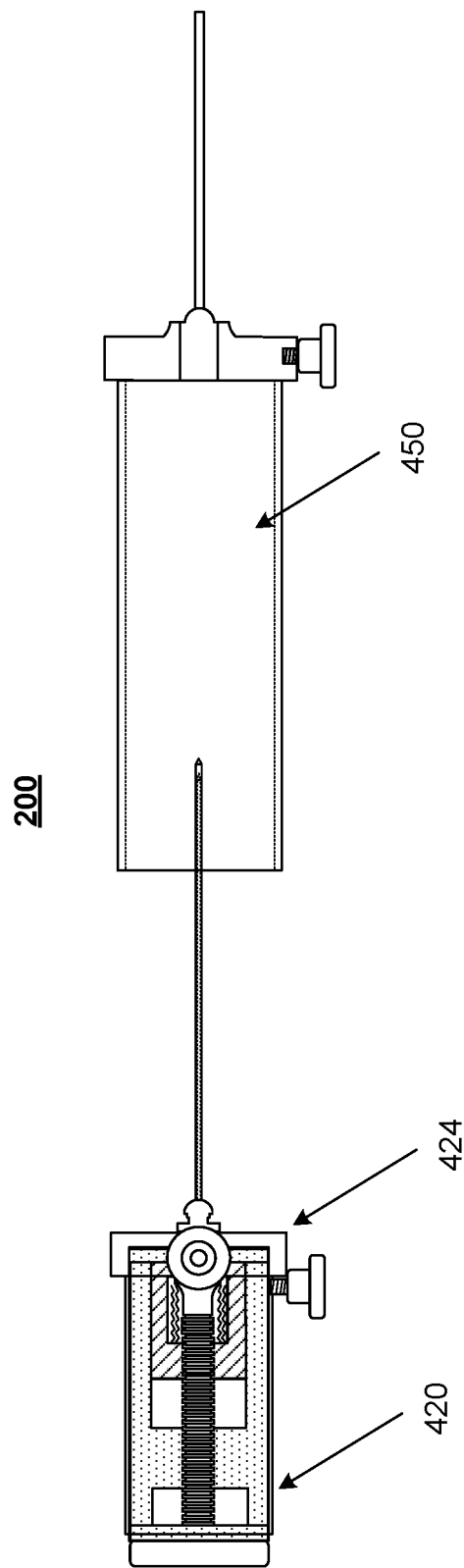
Figure 8C:
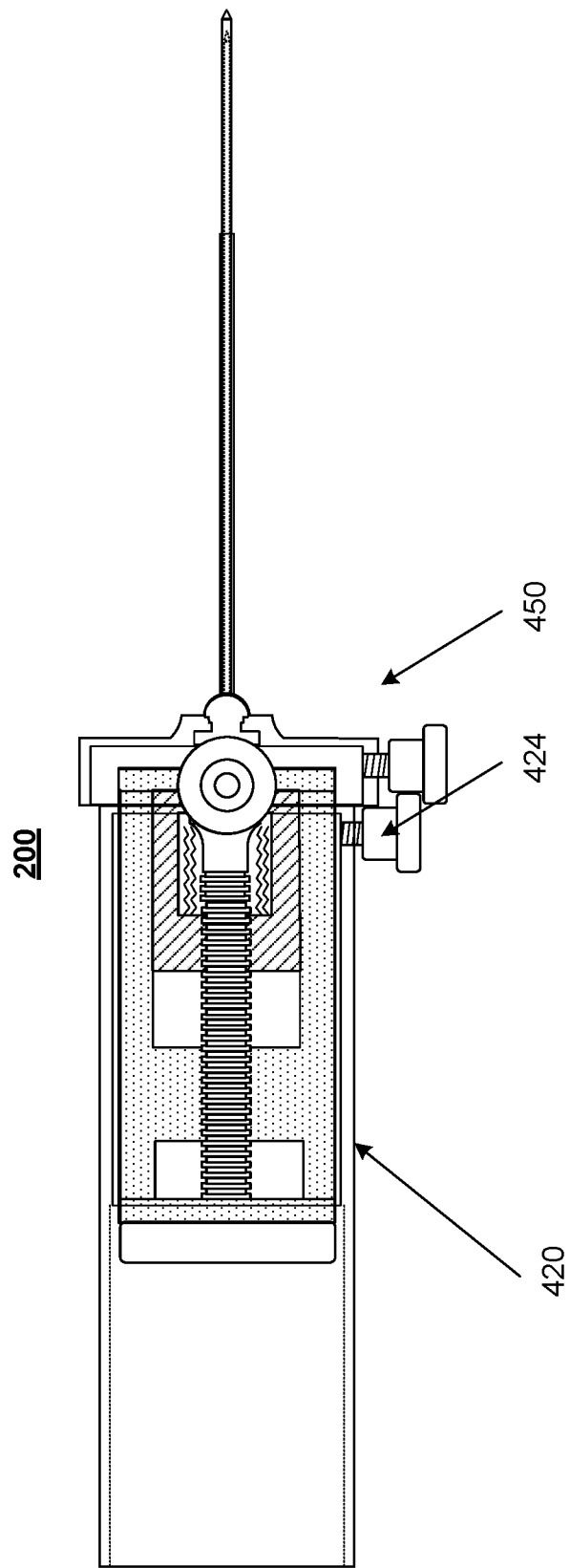

As illustrated in FIGS. 6A and 6B, in this embodiment, plunger control 450 comprises a cylindrical cap 620 moveably attached to a rail 622. Cap 620 is configured to be slidably coupled to rail 622. Thus, cap 620 can slide along rail 622 in either direction of longitudinal axis X. In addition, a screw knob 624 can be tightened (e.g., rotated clockwise to translate the screw toward rail 622, in a first direction along an axis that is perpendicular to longitudinal axis X) through a hole in cap 620 to press fit against rail 624, thereby fixing cap 620 to rail 622. In addition, screw knob 624 can be loosened (e.g., rotated counterclockwise to translate the screw away from rail 622, in an opposing second direction along the axis that is perpendicular to longitudinal axis X), thereby enabling cap 620 to slide with respect to rail 622. Thus, cap 620 can be releasably fixed to rail 622 at any of a range of positions along longitudinal axis X.

In contrast to the embodiment in FIG. 4A, shaft cap 424 is not screwed to shaft 420. Rather, shaft cap 424 comprises a cylindrical cap 610 with a guide 612, into which shaft 420 can be inserted and held. For this purpose, cap 610 comprises a screw knob 614. When shaft 420 is inserted into shaft cap 424, screw knob 614 can be tightened (i.e., rotated clockwise to translate the screw toward shaft 420, in a first direction along an axis that is perpendicular to longitudinal axis X) through a hole in cap 610 to press fit against shaft 420, thereby fixing shaft 420 within shaft cap 424. In addition, screw knob 614 can be loosened (e.g., rotated counterclockwise to translate the screw away from shaft 420, in an opposing second direction along the axis that is perpendicular to longitudinal axis X), thereby unfixing shaft 420 from shaft cap 424.

Guide 612 is configured to slide onto rail 622 of plunger control 450 (e.g., in the same manner as cap 620). Similar to cap 620, guide 612 may comprise a screw knob 616. Screw knob 616 can be tightened (e.g., rotated clockwise to translate the screw toward rail 622, in a first direction along an axis that is perpendicular to longitudinal axis X) through a hole in guide 612 to press fit against rail 624, thereby securing guide 612 to rail 622. In addition, screw knob 616 can be loosened (e.g., rotated counterclockwise to translate the screw away from rail 622, in an opposing second direction along the axis that is perpendicular to longitudinal axis X), thereby enabling guide 612 to slide with respect to rail 622, including off of rail 622. Thus, shaft cap 424 can be releasably fixed to rail 622 at any of a range of positions along longitudinal axis X.

FIGS. 7A-8C illustrate various transparent side and top views of the steerable guide 200 in FIGS. 6A and 6B, in various states of assembly, according to an embodiment. In addition, FIGS. 10A-10D illustrate components of knob 410 and shaft 420. Specifically, shaft 420 may comprise a holding portion 1000 at a proximal end of shaft cavity 426. Holding portion 1000 comprises a through hole that encircles translational screw 430, and comprises one or more protrusions 1010 and/or recesses that mate with corresponding recesses and/or protrusions in translational screw 430. For example, as illustrated in FIG. 10D, translational screw 430 may comprise three longitudinal grooves, which correspond in shape to protrusions 1010, so as to receive protrusions 1010 therein. In addition, knob 410 is fixed (e.g., via one or more screws) to a rotating portion 1020 with a threaded through hole which mates with the threads of translational screw 430. Rotating portion 1020 is held within shaft 420 via a proximal cap 1030 that is fixed between the proximal end surface of shaft 420 and the distal end surface of knob 410. Thus, as knob 410 rotates, rotating portion 1020 rotates within shaft 420 and around translational screw 430, while the mating of protrusions 1010 of holding portion 1000 with the longitudinal grooves in translational screw 430 prevents rotation of translational screw 430 with respect to shaft 420. Consequently, when shaft 420 is held stationary, translational screw 430 moves or translates along longitudinal axis X, through the threaded through hole of rotating portion 1020 fixed to knob 410, without rotating with respect to shaft 420.

FIGS. 11A-11H illustrate a similar operation to the operation described with respect to FIG. 5. It should be understood that these figures represent an exemplary sequence of operations that may be performed in order or reverse order, and which may include additional operations that are not shown. Prior to the illustrated operation, screw knob 624 of plunger control 450 may be tightened (e.g., rotated clockwise) to fix cap 620 at a desired position with respect to rail 622.

As illustrated in FIG. 11A, shaft 420 is positioned within guide 612 of shaft cap 424, so that the needle (i.e., wire 462 and wire tube 464) is positioned within plastic tube 466. In addition, guide 612 of shaft cap 424 is slid onto rail 622 of plunger control 450, so that plastic tube 466 is positioned within rigid outer tube 468, without extending out of the distal end of rigid outer tube 468.

Figure 11B:
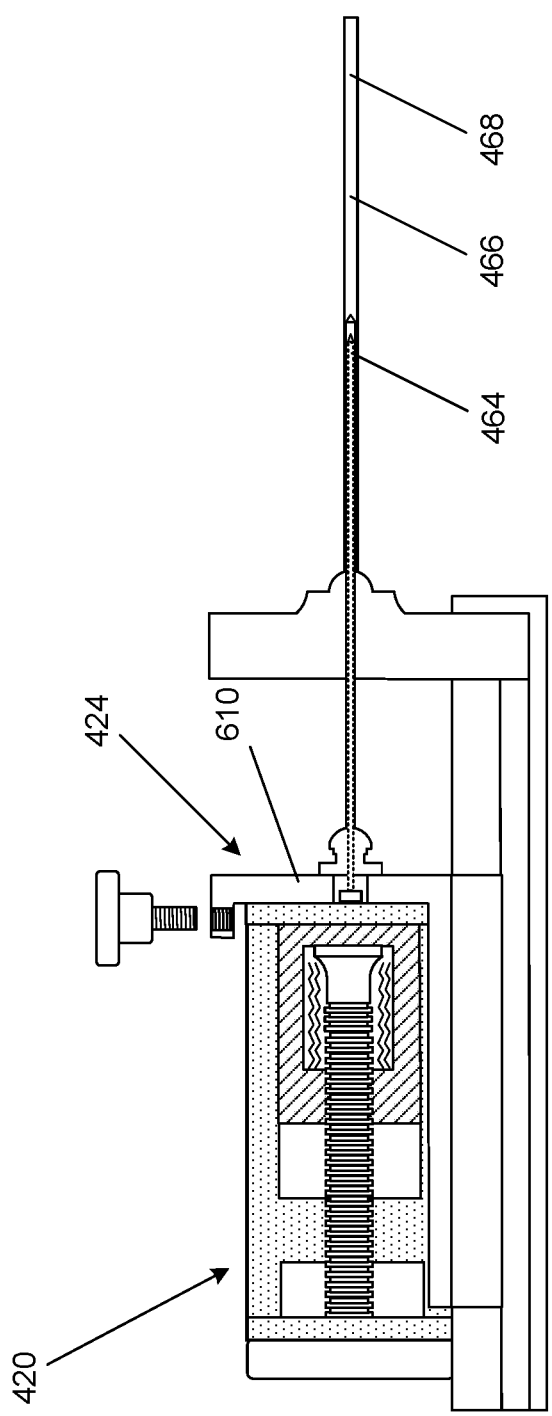

As illustrated in FIG. 11B, shaft 420 is pushed along longitudinal axis X, so that its distal end is flush with the internal proximal surface of cap 610 of shaft cap 424. Shaft cap 424 may be hollow on the proximal end, so that a distal portion of shaft 420 slides into shaft cap 424. Notably, the needle is pushed deeper into plastic tube 466, but plastic tube 466 still does not extend out of the distal end of rigid outer tube 468. At this point, shaft 420 may be rotated to control the azimuth angle of plastic tube 466.

Figure 11C:
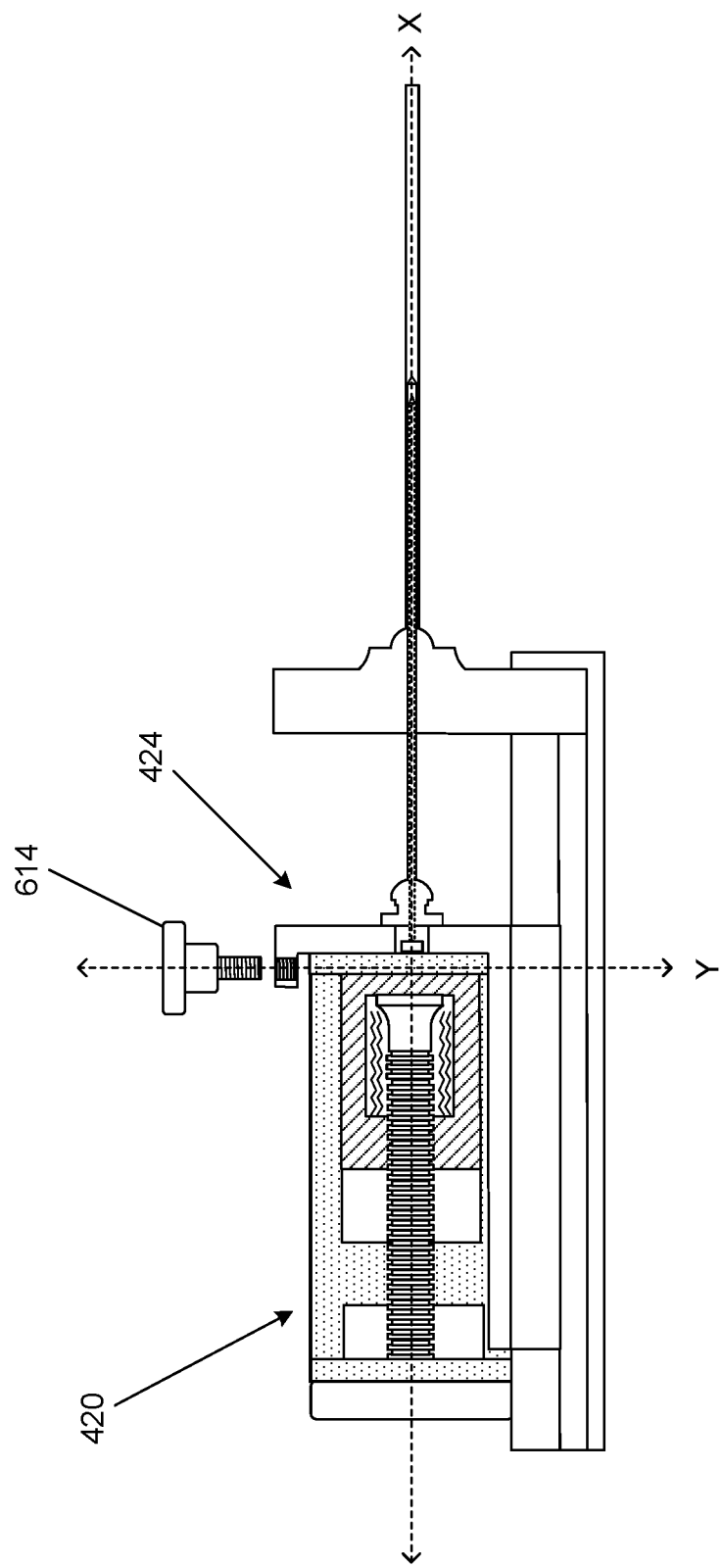
Figure 11D:
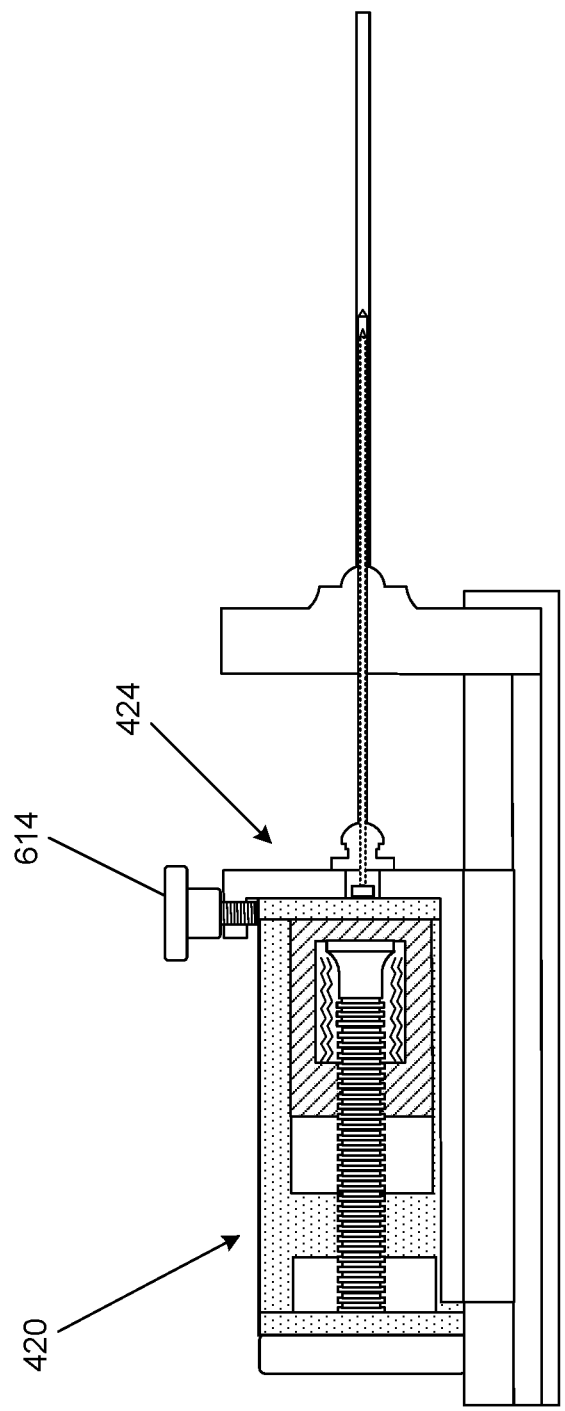

As illustrated in FIGS. 11C and 11D, screw knob 614 is tightened to fix shaft 420 within shaft cap 424. Specifically, screw 614 is tightened (e.g., rotated clockwise), so that a screw translates towards shaft cap 424, along an axis Y, that is orthogonal to longitudinal axis X. Screw knob 614 may be tightened until the end of the screw is pressed against shaft 420, such that shaft 420 is held in place via friction between the end of the screw and shaft 420.

Figure 11E:
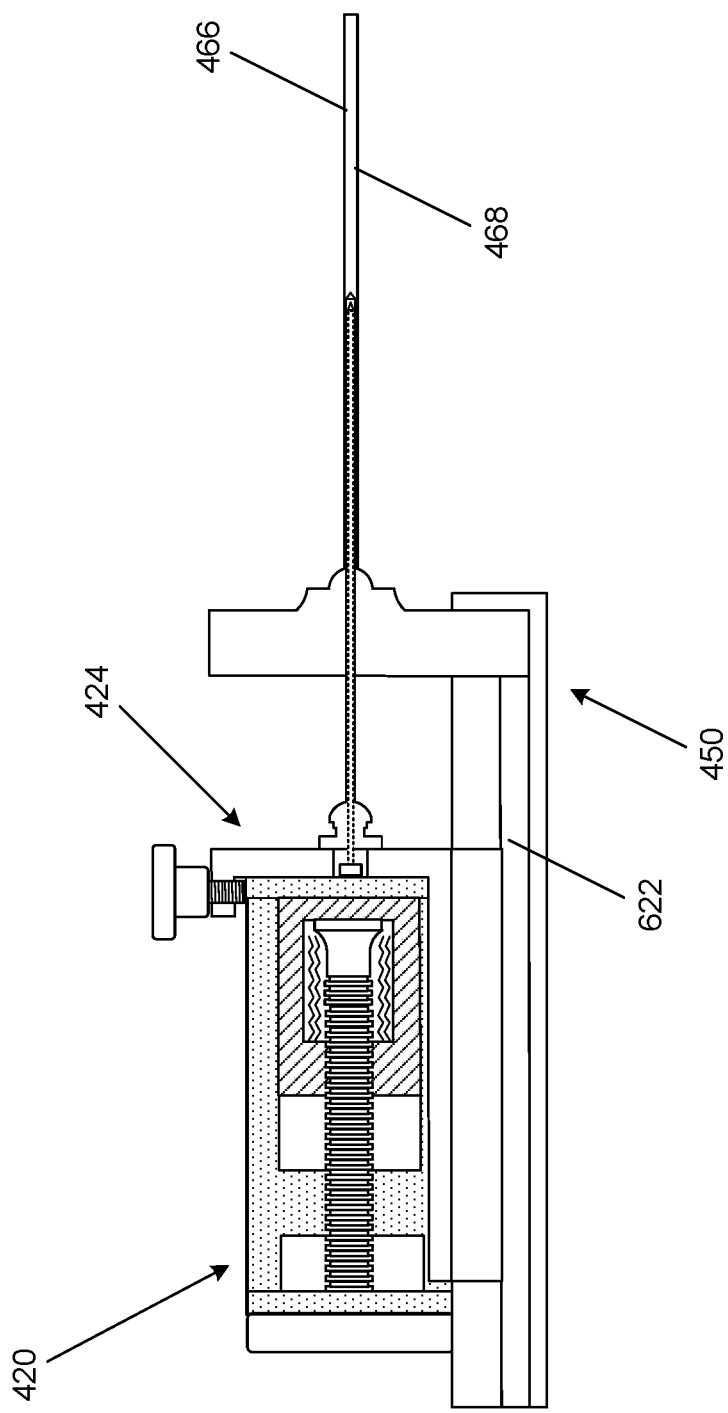

As illustrated in FIG. 11E, shaft cap 424, to which shaft 420 is affixed, is slid distally along rail 622 of plunger control 450, so that the tip of plastic tube 466 extends slightly beyond the distal tip of rigid outer tube 468. Notably, at this time, plastic tube 466 is still linear.

Figure 11F:
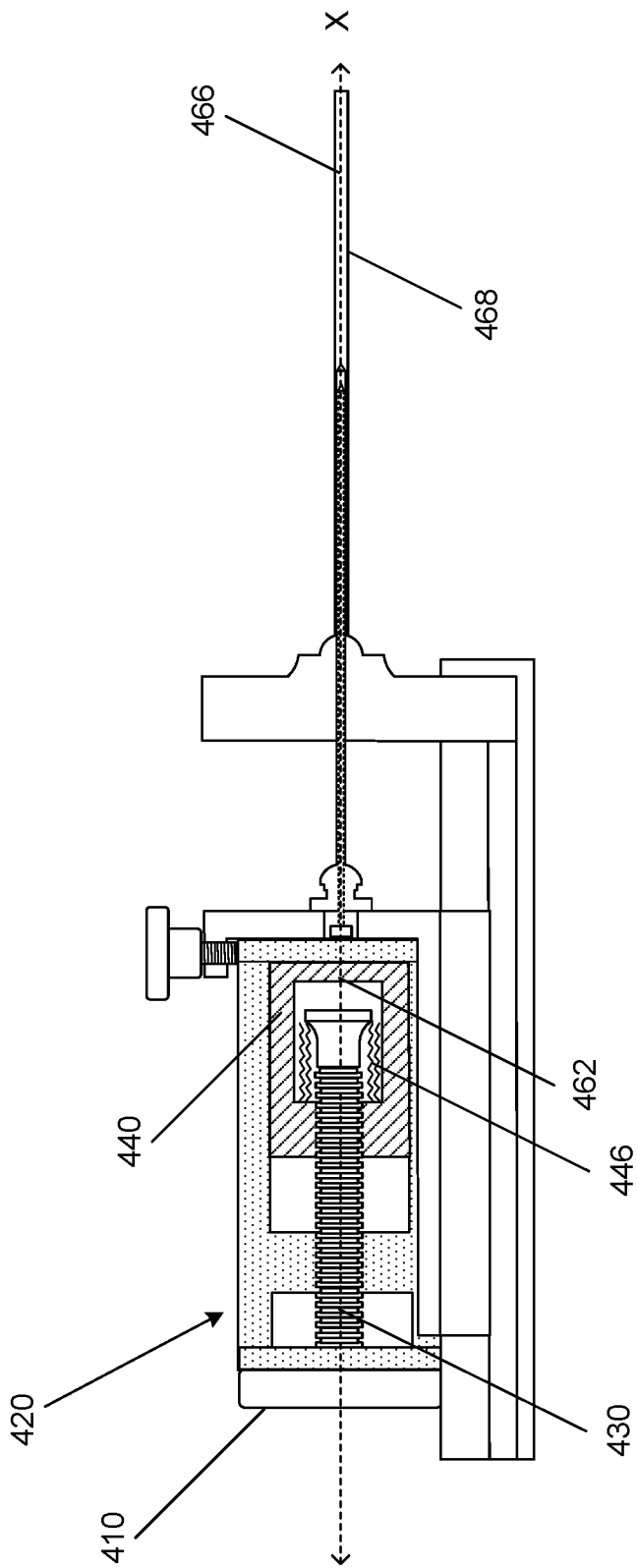

As illustrated in FIG. 11F, knob 410 is rotated to retract translational screw 430 proximally along longitudinal axis X. When the tension applied to knob 410 is greater than the spring force of spring 446, continued translation of translational screw 430, in the proximal direction along longitudinal axis X, will cause spring 446 to compress proximally, since spring housing 440 is held in place by wire 462. Spring 446 stores the tension that would otherwise be applied to wire 462, thereby relieving the pressure that would otherwise damage the needle, plastic tube 466, and/or rigid outer tube 468. As discussed elsewhere herein, the amount of compression that is applied to spring 446 corresponds to the amount of curvature that will be applied to the needle—and therefore, plastic tube 466—when they exit rigid outer tube 468.

Figure 11G:
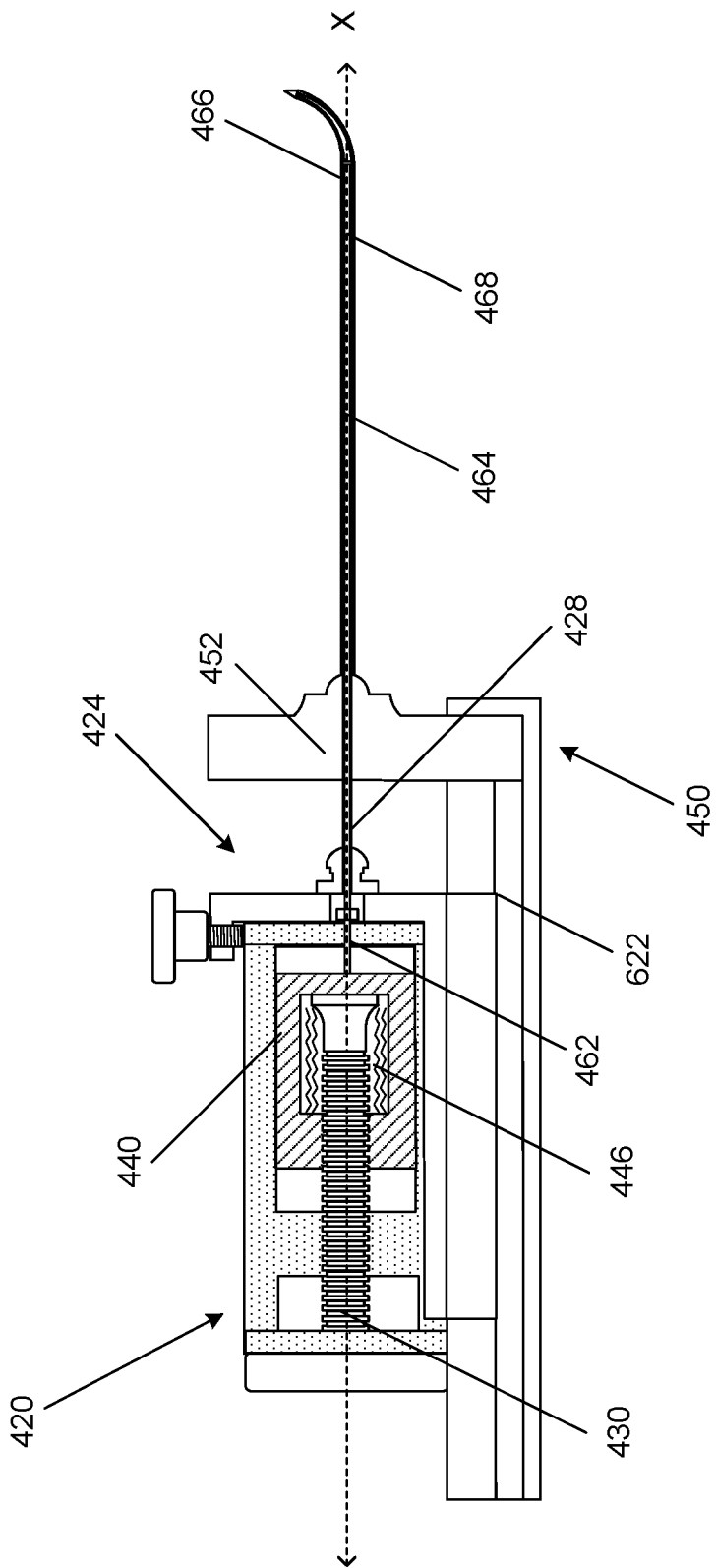
Figure 11H:
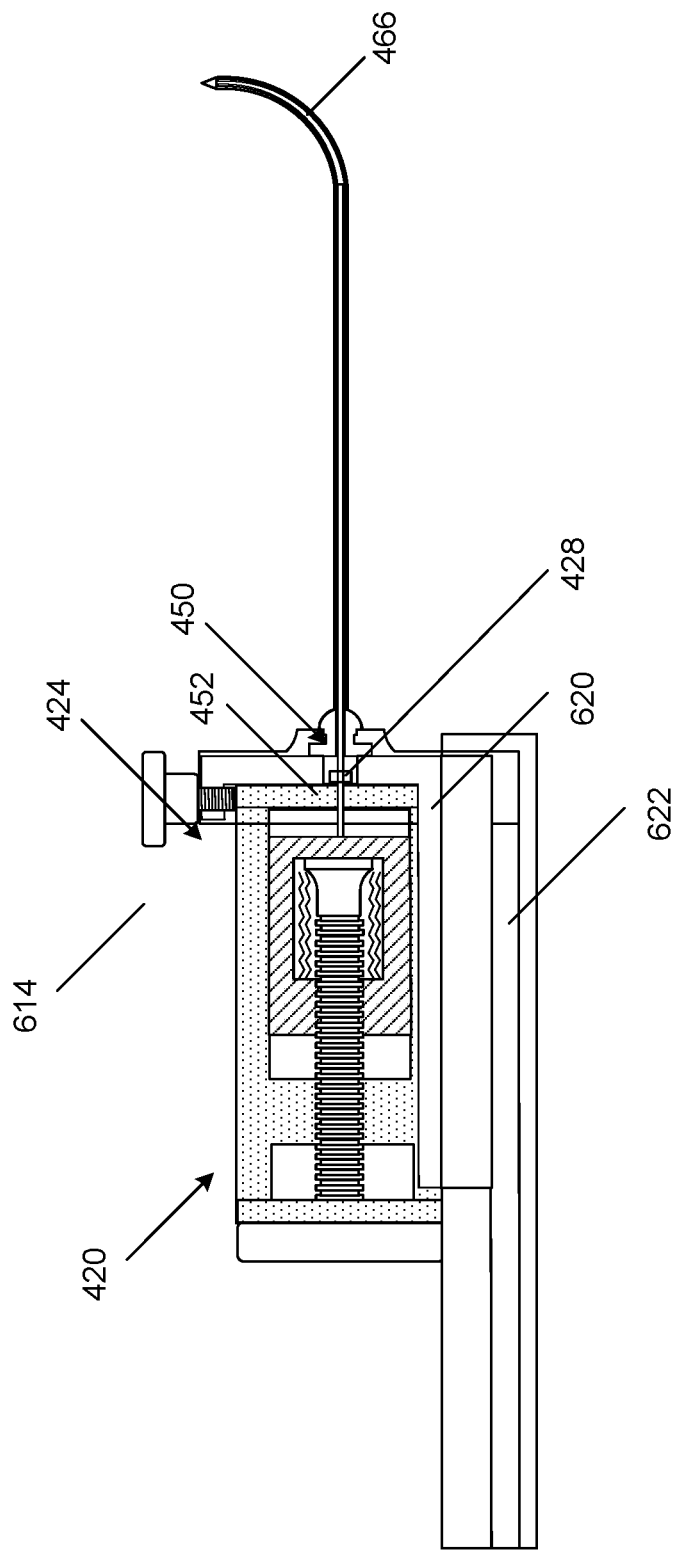

As illustrated in FIGS. 11G and 11H, as shaft cap 424, with affixed shaft 420, is slid distally along rail 622 of plunger control, such that plastic tube 466 is pushed farther beyond the distal tip of rigid outer tube 468, spring 446 decompresses. Since the distal end of spring 446 is held in place by translational screw 430, spring 446 decompresses proximally, causing spring housing 440 to translate proximally along longitudinal axis X. Since wire 462 is fixed to spring housing 440, wire 462 is pulled proximally relative to wire tube 464. This causes the needle to curve within plastic tube 466 (e.g., by virtue of one or more notches in the distal end of wire tube 464), thereby causing plastic tube 466 to curve gradually as shaft cap 424 is slid distally.

Eventually, as shown in FIG. 11H, when shaft cap 424 is flush against cap 620 of plunger control 450, plastic tube 466 is fully extended from rigid outer tube 468, at the curvature set by the compression of spring 446. Notably, when shaft cap 424 is flush with cap 620, tube holder 428 is positioned within a recess 452 in the proximal surface of plunger control 450. Screw knob 616 may be tightened at this point to fix the position of shaft cap 424 with respect to rail 622.

At the point shown in FIG. 11H, screw knob 614 may be loosened (e.g., rotated counterclockwise), to unfix shaft 420 from shaft cap 424. Then, shaft 420, along with the needle (i.e., wire 462 and wire tube 464), may be retracted proximally and removed. Notably, since plastic tube 466 is connected to shaft cap 424, which is fixed to rail 622 via screw knob 616, plastic tube 466 will remain within the insertion path with its distal tip at the target site. Accordingly, a fiber optical cable may be inserted through plastic tube 466 to perform ablation at the target site. When the ablation is complete, shaft cap 424 may be unfixed from plunger control 450 by loosening screw knob 616. Then, shaft cap 424 may be slid proximally off of rail 622, thereby removing plastic tube 466 (e.g., along with the fiber optic cable) from the subject.

While the embodiments described herein have been primarily described with respect to a manual system (e.g., manual knobs for setting curvature, manual rotation, manual translation), it should be understood that steerable guide 200 may be adapted for an automated system. For example, the curvature, rotation, and translation may be set and controlled by a robotic navigational system with mechanical movements driven by motors or other actuators, under the control of a computer (e.g., comprising a central processing unit (CPU) or other hardware processor, memory, an input/output interface, and/or the like).

The above description of the disclosed embodiments is provided to enable any person skilled in the art to make or use the invention. Various modifications to these embodiments will be readily apparent to those skilled in the art, and the general principles described herein can be applied to other embodiments without departing from the spirit or scope of the invention. Thus, it is to be understood that the description and drawings presented herein represent a presently preferred embodiment of the invention and are therefore representative of the subject matter which is broadly contemplated by the present invention. It is further understood that the scope of the present invention fully encompasses other embodiments that may become obvious to those skilled in the art and that the scope of the present invention is accordingly not limited.

Combinations, described herein, such as "at least one of A, B, or C," "one or more of A, B, or C," "at least one of A, B, and C," "one or more of A, B, and C," and "A, B, C, or any combination thereof" include any combination of A, B, and/or C, and may include multiples of A, multiples of B, or multiples of C. Specifically, combinations such as "at least one of A, B, or C," "one or more of A, B, or C," "at least one of A, B, and C," "one or more of A, B, and C," and "A, B, C, or any combination thereof" may be A only, B only, C only, A and B, A and C, B and C, or A and B and C, and any such combination may contain one or more members of its constituents A, B, and/or C. For example, a combination of A and B may comprise one A and multiple B's, multiple A's and one B, or multiple A's and multiple B's.

What is claimed is:

1. A steerable guide comprising:
   a needle comprising a wire tube and a wire within the wire tube, wherein the wire is fixed to a tip of the needle so as to curve the needle when retracted relative to the wire tube;
   a shaft with a proximal end and a distal end, wherein the shaft comprises a shaft cavity, and wherein the wire tube is connected to the distal end of the shaft;
   a spring housing with a proximal end and a distal end, wherein the spring housing is within the shaft cavity, wherein the spring housing comprises a spring cavity and a spring within the spring cavity, and wherein the wire is connected to the distal end of the spring housing; and
   a translational screw extending through the proximal end of the shaft into the shaft cavity and through a proximal end of the spring housing into the spring cavity, such that a distal end of the translational screw is within the spring cavity, wherein the translational screw is configured to move in each of a proximal direction and a distal direction along a longitudinal axis of the shaft;
wherein the spring is positioned, within the spring cavity, between the proximal end of the spring housing and the distal end of the translational screw, such that, when the translational screw moves in the proximal direction while a position of the spring housing is fixed, the spring is compressed between the proximal end of the spring housing and the distal end of the translational screw.

2. The steerable guide of claim 1, further comprising a knob, attached to the shaft and configured to rotate around the translational screw in each of two rotational directions around the longitudinal axis so as to actuate movement of the translational screw in both the proximal direction and the distal direction.

3. The steerable guide of claim 1, wherein the wire comprises nitinol.

4. The steerable guide of claim 1, wherein the wire tube comprises nitinol.

5. The steerable guide of claim 1, wherein the wire tube comprises one or more notches in at least one side of the wire tube, wherein the one or more notches compress or elongate in response to movement of the wire.

6. The steerable guide of claim 5, wherein the one or more notches comprises at least nine notches.

7. The steerable guide of claim 1, wherein the spring comprises thermoplastic polyurethane.

8. The steerable guide of claim 1, further comprising an outer sheath releasably fixed to a distal end of a shaft cap and configured to receive the needle through its proximal end, wherein the shaft cap is configured to attach to the distal end of the shaft.

9. The steerable guide of claim 8, wherein the shaft cap is configured to releasably attach to the distal end of the shaft.

10. The steerable guide of claim 8, wherein the outer sheath is closed at its distal end.

11. The steerable guide of claim 8, wherein an outer diameter of the outer sheath is less than 1.1 millimeters.

12. The steerable guide of claim 8, wherein the outer sheath comprises ethyl vinyl acetate.

13. The steerable guide of claim 8, wherein the outer sheath is releasably fixed to the distal end of the shaft cap indirectly by being fixed to a tube holder that is releasably fixed to the distal end of the shaft cap.

14. The steerable guide of claim 8, further comprising a plunger control configured to receive the shaft cap, such that the shaft cap is capable of sliding relative to the plunger control in both the proximal direction and the distal direction.

15. The steerable guide of claim 14, further comprising a rigid outer tube connected to a distal end of the plunger control, wherein the rigid outer tube is configured to receive the outer sheath through its proximal end, and wherein the outer sheath is longer than the rigid outer tube, such that, when the shaft cap is slid in the proximal direction relative to the plunger control, the outer sheath is retracted into the rigid outer tube, and, when the shaft is slid in the distal direction relative to the plunger control, the outer sheath is extended out of a distal end of the rigid outer tube.

16. The steerable guide of claim 15, wherein an outer diameter of the rigid outer tube is less than 2.5 millimeters.

17. The steerable guide of claim 15, wherein the rigid outer tube comprises nonferrous stainless steel.

18. The steerable guide of claim 1, wherein the translational screw comprises one or more longitudinal grooves that extend parallel to the longitudinal axis of the shaft, wherein the shaft comprises a holding portion on a proximal end of the shaft cavity, and wherein the holding portion comprises a through hole with one or more protrusions that are configured to fit within the one or more longitudinal grooves, so as to prevent the translational screw from rotating relative to the shaft.

19. A method of operating the steerable guide of claim 15, comprising:
while the outer sheath is fully retracted into the rigid outer tube with the needle positioned within the outer sheath, actuating the translational screw to move the translational screw in the proximal direction, so as to at least partially compress the spring, according to a planned curvature amount;
moving the shaft cap with the shaft, in the distal direction relative to the plunger control, so as to extend the outer sheath, with the needle positioned within the outer sheath, out of the rigid outer tube, such that the spring decompresses in the proximal direction, thereby pushing the spring housing in the proximal direction relative to the shaft cavity, thereby retracting the wire in the proximal direction relative to the shaft cavity, thereby causing the needle to curve to the planned curvature amount, thereby causing the outer sheath around the needle to curve to the planned curvature amount.

20. The method of claim 19, further comprising:
continuing to move the shaft cap with the shaft in the distal direction until a distal tip of the outer sheath is at a target position;
retracting the shaft, so as to retract the needle from the outer sheath, while the shaft cap remains in place;
inserting a fiber optic cable into the outer sheath, such that a distal tip of the fiber optic cable is positioned at the distal tip of the outer sheath; and
performing ablation at the target position via the fiber optic cable, while running coolant through the outer sheath.

21. The method of claim 19, wherein a spring constant of the spring is set such that the needle gradually curves to the predetermined curvature amount as the needle is extended out of the rigid outer tube.

* * * * *